(12) United States Patent
Cook et al.

(10) Patent No.: US 11,678,995 B2
(45) Date of Patent: Jun. 20, 2023

(54) MAGNETIC INTERVERTEBRAL DISC REPLACEMENT DEVICES AND METHODS THEREOF

(71) Applicant: Fellowship of Orthopaedic Researchers, Inc., Metairie, LA (US)

(72) Inventors: Stephen D. Cook, Metairie, LA (US); Michael C. Harrison, Metairie, LA (US); Liam P. Nolan, New Orleans, LA (US); Laura P. Patron, Belle Chase, LA (US); Samantha L. Salkeld, Metairie, LA (US)

(73) Assignee: Fellowship of Orthopaedic Researchers, Inc., Metairie, LA (US)

( * ) Notice: Subject to any disclaimer, the term of this patent is extended or adjusted under 35 U.S.C. 154(b) by 57 days.

(21) Appl. No.: 16/361,980

(22) Filed: Mar. 22, 2019

(65) Prior Publication Data
US 2020/0022818 A1  Jan. 23, 2020

Related U.S. Application Data

(60) Provisional application No. 62/701,518, filed on Jul. 20, 2018.

(51) Int. Cl.
*A61F 2/44* (2006.01)

(52) U.S. Cl.
CPC ...... *A61F 2/4425* (2013.01); *A61F 2002/443* (2013.01); *A61F 2220/0025* (2013.01);
(Continued)

(58) Field of Classification Search
CPC ............. A61F 2/4425; A61F 2002/443; A61F 2002/30079; A61F 2210/009;
(Continued)

(56) References Cited

U.S. PATENT DOCUMENTS 4,024,588 A  5/1977  Janssen et al.
4,332,037 A  6/1982  Esformes et al.
(Continued)

FOREIGN PATENT DOCUMENTS

DE  2821678 A1  11/1979

OTHER PUBLICATIONS

International Search Report and Written Opinion by the International Searching Authority in PCT Application No. PCT/US2013/50929, dated Oct. 31, 2013.

*Primary Examiner* — Anu Ramana
(74) *Attorney, Agent, or Firm* — Grimes & Yvon LLP

(57) ABSTRACT

An intervertebral disc replacement device comprising a superior plate and an inferior plate, in which each plate contains one or more embedded magnets. The one or more magnets in the superior plate and the one or more magnet in the inferior plate are oriented such that a magnetic force exists between the one or more magnets in the superior plate and the one or more magnet in the inferior plate. In addition, an intervertebral disc replacement device comprising a superior plate and an inferior plate, in which each plate contains one or more embedded magnets, and the plates are designed to form an articulating surface. Further, an intervertebral disc replacement device comprising a superior plate, an inferior plate, and a spacer, in which each plate contains one or more embedded magnets, and the superior and inferior plates are designed to form articulating surfaces with the spacer.

14 Claims, 20 Drawing Sheets

(52) U.S. Cl.
CPC ............... *A61F 2310/00029* (2013.01); *A61F 2310/00059* (2013.01); *A61F 2310/00089* (2013.01)

(58) Field of Classification Search
CPC .. A61F 2310/00029; A61F 2310/00059; A61F 2310/00089
See application file for complete search history.

(56) References Cited

U.S. PATENT DOCUMENTS

| | | | |
|---|---|---|---|
| 5,595,563 A * | 1/1997 | Moisdon | A61B 17/8866 600/12 |
| 5,879,386 A | 3/1999 | Jore | |
| 6,387,096 B1 | 5/2002 | Hyde | |
| 6,500,178 B2 | 12/2002 | Zucherman et al. | |
| 6,599,321 B2 | 7/2003 | Hyde | |
| 6,695,619 B2 | 2/2004 | Brown-Wilkinson | |
| 7,101,374 B2 * | 9/2006 | Hyde, Jr. | A61B 17/68 606/60 |
| 7,195,645 B2 | 3/2007 | Disilvestro et al. | |
| 7,531,002 B2 * | 5/2009 | Sutton | A61F 2/442 623/18.12 |
| 7,637,927 B2 | 12/2009 | Hyde | |
| 7,717,959 B2 | 5/2010 | William et al. | |
| 8,029,570 B2 | 10/2011 | Barnes et al. | |
| 8,114,158 B2 | 2/2012 | Carl et al. | |
| 8,118,815 B2 * | 2/2012 | van der Walt | A61B 17/1764 606/88 |
| 8,449,615 B2 | 5/2013 | Fleischmann | |
| 8,801,796 B2 | 8/2014 | Rogachefsky | |
| 9,289,311 B1 | 3/2016 | Whipple | |
| 9,408,714 B1 * | 8/2016 | Whipple | A61F 2/4425 |
| 2002/0161447 A1 * | 10/2002 | Salehi | A61F 2/3868 623/20.28 |
| 2003/0187510 A1 | 10/2003 | Hyde | |
| 2003/0195633 A1 | 10/2003 | Hyde | |
| 2004/0106995 A1 | 6/2004 | Le Couedic et al. | |
| 2005/0234555 A1 * | 10/2005 | Sutton | A61F 2/4455 623/17.15 |
| 2005/0251080 A1 | 11/2005 | Hyde | |
| 2006/0036323 A1 | 2/2006 | Carl et al. | |
| 2006/0079897 A1 | 4/2006 | Harrison et al. | |
| 2006/0247782 A1 | 11/2006 | Molz et al. | |
| 2006/0282166 A1 * | 12/2006 | Molz | A61L 27/28 623/17.13 |
| 2007/0050030 A1 | 3/2007 | Kim | |
| 2007/0100457 A1 | 5/2007 | Hyde | |
| 2007/0162134 A1 | 7/2007 | Marnay et al. | |
| 2007/0179493 A1 * | 8/2007 | Kim | A61B 17/7062 606/33 |
| 2007/0233251 A1 | 10/2007 | Abdou | |
| 2008/0234733 A1 | 9/2008 | Scrantz et al. | |
| 2008/0306324 A1 | 12/2008 | Bonutti et al. | |
| 2009/0024166 A1 | 1/2009 | Carl et al. | |
| 2009/0048618 A1 | 2/2009 | Harrison et al. | |
| 2009/0318976 A1 | 12/2009 | Gabriel et al. | |
| 2010/0030337 A1 | 2/2010 | Ari et al. | |
| 2010/0036493 A1 | 2/2010 | Simon | |
| 2010/0121381 A1 | 5/2010 | Berta et al. | |
| 2010/0234954 A1 * | 9/2010 | Justis | A61F 2/4425 623/17.12 |
| 2010/0280551 A1 | 11/2010 | Pool et al. | |
| 2011/0022091 A1 | 1/2011 | Anderson et al. | |
| 2011/0029020 A1 | 2/2011 | Gordon et al. | |
| 2011/0257749 A1 | 10/2011 | Fleischmann | |
| 2011/0257754 A1 | 10/2011 | Fleischmann | |
| 2012/0035661 A1 | 2/2012 | Pool et al. | |
| 2013/0144340 A1 | 6/2013 | Sheffer et al. | |
| 2013/0165975 A1 | 6/2013 | Tebbe et al. | |
| 2013/0310937 A1 | 11/2013 | Pimenta | |
| 2014/0025122 A1 | 1/2014 | Cook et al. | |
| 2014/0142700 A1 | 5/2014 | Donner et al. | |
| 2015/0005886 A1 | 1/2015 | Pinneo | |
| 2018/0014838 A1 | 1/2018 | Ning | |
| 2019/0021776 A1 | 1/2019 | Archbold | |
| 2019/0053864 A1 | 2/2019 | Cook et al. | |

* cited by examiner

MAGNETIC INTERVERTEBRAL DISC REPLACEMENT DEVICES AND METHODS THEREOF

CROSS-REFERENCE TO RELATED APPLICATIONS

This application claims the benefit of U.S. Provisional Application Ser. No. 62/701,518 filed on Jul. 20, 2018, the entirety of which is herein incorporated by reference.

FIELD OF INVENTION

The present invention relates generally to prosthetic devices and their use. In particular, the present invention relates to devices containing magnets for use in replacing intervertebral discs.

BACKGROUND OF THE INVENTION

The spine provides the primary support for the body and is comprised of 33 individual bones, or vertebrae. The spine is divided into five regions: the cervical, thoracic, and lumbar regions, which are made up of 24 vertebrae that are movable; and the sacral and coccygeal regions, which comprise 9 vertebrae that are fused or unmovable. As shown in FIGS. 1A and 1B, each vertebra 1 consists of a vertebral body 3, a vertebral arch 5, and posterior processes 7 that extend from the vertebral arch 5. The movable vertebrae are stacked in series and are separated and cushioned by an intervertebral disc 20. The unit formed by two adjacent vertebrae and the intervertebral disc therebetween (along with adjoining ligaments) is referred to as a "motion segment" or "spine segment" 15, and it is regarded as the smallest physiological motion unit of the spine to exhibit biomechanical characteristics that are similar to those of the entire spine.

Each movable vertebra transmits loads to adjacent bodies via the intervertebral disc 20 and two posterior facet joints 9. The intervertebral disc 20 is composed of an annulus or outer ring of fibrous tissue 23 and the nucleus pulposus 25, which is a gel-like substance contained within the annulus 23 and between the cartilaginous endplates (not shown) of the adjacent vertebral bodies 3. In a healthy disc, the nucleus pulposus 25 acts as an incompressible fluid and forms a hard sphere-like structure within the nuclear recess or fossa (not shown) of the endplates, resembling a fulcrum to give mobility to the spine. Stability of the spine is achieved by balancing loads in the intervertebral disc 20 and the two facet joints 9.

Degenerative disc disease affects the physiology and function of the intervertebral disc and may be caused by aging, protrusion of the nucleus pulposus into the annulus or endplates, trauma, arthritis, or other causes. The result of the disease is a change in the biomechanical properties of the disc, often including a reduction in disc height that alters the loading pattern of the disc. Degeneration of the disc also frequently results in degeneration of the facet joints, loss of stability of the motion segment, and compression of the nerves branching out of the spinal column. Compression of these nerves can cause clinical symptoms including pain.

Surgical treatments for degenerative disc disease include discectomy (surgical removal of abnormal intervertebral disc material), fusion (surgical technique that joins two or more vertebrae), and others. However, these treatments are not without problems and complications. Discectomy and fusion can alter the biomechanics of the motion segment and can often lead to degeneration of the adjacent motion segments. And even though a segment is fused or motion is prevented, pain and clinical symptoms frequently persist. For this reason, replacement of the intervertebral disc, which aims to preserve and restore normal motion to the spine segment, has emerged as an important treatment option.

Although first used in Europe in the 1980's, disc replacement was not approved in the United States by the FDA until 2004. There are now a number of different disc designs available for use in disc replacement surgery, but all have the same goal of reproducing the size (height) and function (range of motion) of the normal intervertebral disc. Materials that can be used in the construction of disc replacements include medical grade plastics (primarily polyethylene and polyetheretherketone (PEEK)), metals (primarily cobalt chromium and titanium alloys), and ceramics (including aluminum oxide, zirconia, and others).

Disc designs include two-piece designs consisting of two plates that attach to the adjacent vertebral bodies and that have surfaces which articulate against each other, such as a cup-and-dish configuration. These types of devices often have a polymeric surface and a metallic surface that articulate, but metal/metal and polymer/polymer devices have also been available. The polymeric surface(s) may be contained within a metal shell, which provides a surface optimized for attachment to the vertebral body endplates. Alternatively, disc replacements may have a three-piece design, containing two plates (usually metallic) that attach to the vertebral endplates, and a soft, usually polymeric, spacer that articulates between the two surfaces.

Problems associated with current intervertebral disc replacements are similar to those seen in other arthroplasty or joint replacement devices such as total hip and knee replacement devices. These problems include failure of the plates of the device to attach to the endplates of the vertebrae and/or loosening of the interface. This can be the result of the constraining nature of the articulation, excessive wear and wear debris generated at the articulating surfaces, and, in the case of a three-piece device, dislocation or dissociation of the polymeric spacer between the two plates.

Thus, there remains a need for an intervertebral disc replacement device that will maintain stable attachment to adjacent vertebrae and provide normal biomechanics to the motion segment.

SUMMARY OF INVENTION

The present invention relates to intervertebral disc replacement devices and methods for their use in treating or preventing degenerative disc disease.

An aspect of the invention relates to an intervertebral disc replacement device that comprises a first, or "superior," plate and a second, or "inferior," plate, in which each plate contains one or more magnets. Each plate comprises a fixation surface, an inner surface, and an edge surface. The magnet(s) in the superior plate and the magnet(s) in the inferior plate are oriented such that a magnetic force exists between the magnet(s) in the superior plate and the magnet(s) in the inferior plate. In some embodiments, the magnetic force is repulsive. In some embodiments, the fixation surface of the superior plate and/or the inferior plate comprises a surface geometry or a surface feature that helps adhere the plate to a vertebra endplate. In some embodiments, the fixation surface, the inner surface, or both, of the superior plate and/or the inferior plate may be flat or may comprise a curvature. In certain embodiments, a linking material is attached to both the superior plate and the inferior plate.

An aspect of the invention relates to an intervertebral disc replacement device that comprises a superior plate and an inferior plate, in which each plate contains one or more magnets. Each plate comprises a fixation surface, an articulating surface, and an edge surface. The articulating surface of the superior plate is configured to articulate against the articulating surface of the inferior plate. The magnet(s) in the superior plate and the magnet(s) in the inferior plate are oriented such that a magnetic force exists between the magnet(s) in the superior plate and the magnet(s) in the inferior plate. In some embodiments, the magnetic force is repulsive. In some embodiments, the fixation surface of the superior plate and/or the inferior plate comprises a surface geometry or a surface feature that helps adhere the plate to a vertebra endplate.

Another aspect of the invention relates to an intervertebral disc replacement device that comprises a superior plate, an inferior plate, and a spacer positioned between the superior and inferior plates. The superior and inferior plates each comprise a fixation surface, an articulating surface, and an edge surface, and the spacer comprises a superior articulating surface, an inferior articulating surface, and an edge surface. The articulating surface of the superior plate is configured to articulate against the superior articulating surface of the spacer, and the articulating surface of the inferior plate is configured to articulate against the inferior articulating surface of the spacer. In some embodiments, each plate contains one or more magnets, and, in certain embodiments, the magnet(s) in each of the plates are oriented such that a magnetic force exists between the magnet(s) of the superior plate and the magnet(s) of the inferior plate. In other embodiments, each plate and the spacer contain one or more magnets and, in certain embodiments, the magnet(s) in each of the plates and the spacer are oriented such that a magnetic force exists between the magnet(s) of the superior plate and the magnet(s) of the spacer, and/or between the magnet(s) of the inferior plate and the magnet(s) of the spacer. The magnetic force may be repulsive or attractive. In some embodiments, the fixation surface of the superior plate and/or the inferior plate comprises a surface geometry or a surface feature that helps adhere the plate to a vertebra endplate.

A further aspect of the invention relates to (i) a method of treating degenerative disc disease in an intervertebral disc, (ii) a method of relieving pain caused by degenerative disc disease in an intervertebral disc, or (iii) a method of reducing pain caused by degenerative disc disease in an intervertebral disc; these methods comprise implanting an intervertebral disc replacement device described above.

BRIEF DESCRIPTION OF THE DRAWING FIGURES

The present disclosure will be further explained with reference to the attached drawing figures, wherein like structures are referred to by like numerals throughout the several views. The drawing figures shown are not necessarily to scale, with emphasis instead generally being placed upon illustrating the principles of the present disclosure, and some features may be exaggerated to show details of particular components. In addition, any measurements, specifications and the like shown in the drawing figures, or described below, are intended to be illustrative, and not restrictive. Therefore, specific structural and functional details disclosed herein are not to be interpreted as limiting, but merely as a representative basis for teaching one skilled in the art to variously employ the intervertebral disc replacement devices, and methods thereof.

FIG. 1A is a lateral view of the motion segment, and FIG. 1B is an anterior view of the motion segment.

FIG. 2A is a lateral view of the device, and FIG. 2B is an anterior view of the device.

FIG. 3A is a lateral view of the device, and FIG. 3B is an anterior view of the device.

FIG. 4A is a lateral view of the device, and FIG. 4B is an anterior view of the device.

FIG. 5A is a lateral view of the device, and FIG. 5B is an anterior view of the device.

FIG. 6A is lateral view of the device implanted into the motion segment, and FIG. 6B is an anterior view of the device implanted into the motion segment.

Figure 7A:
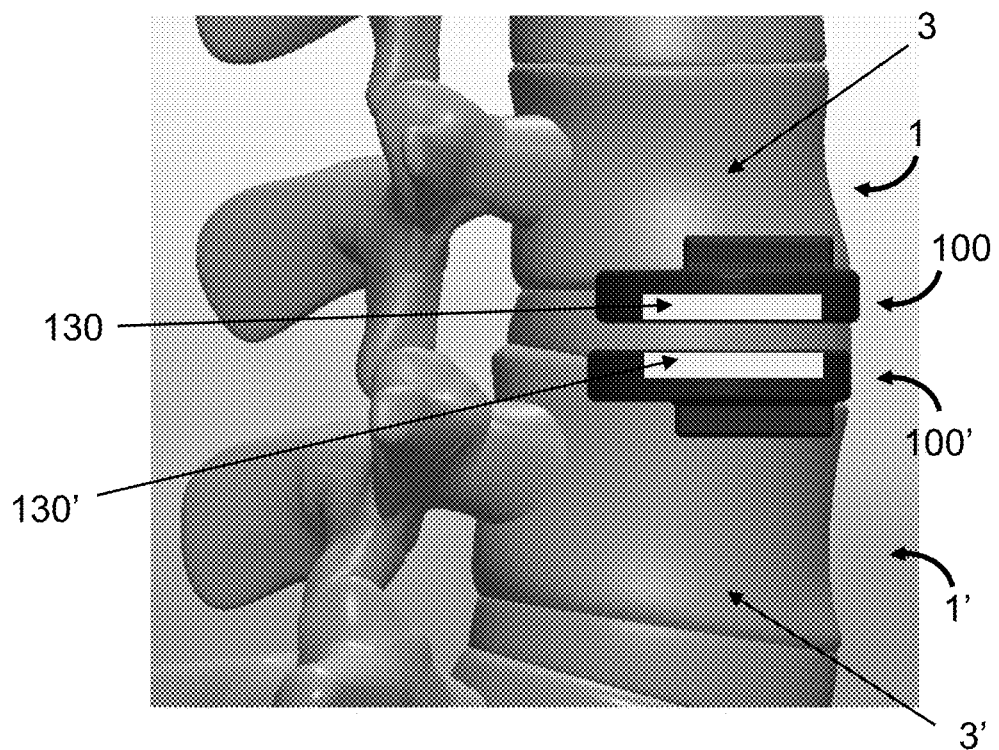
Figure 7B:
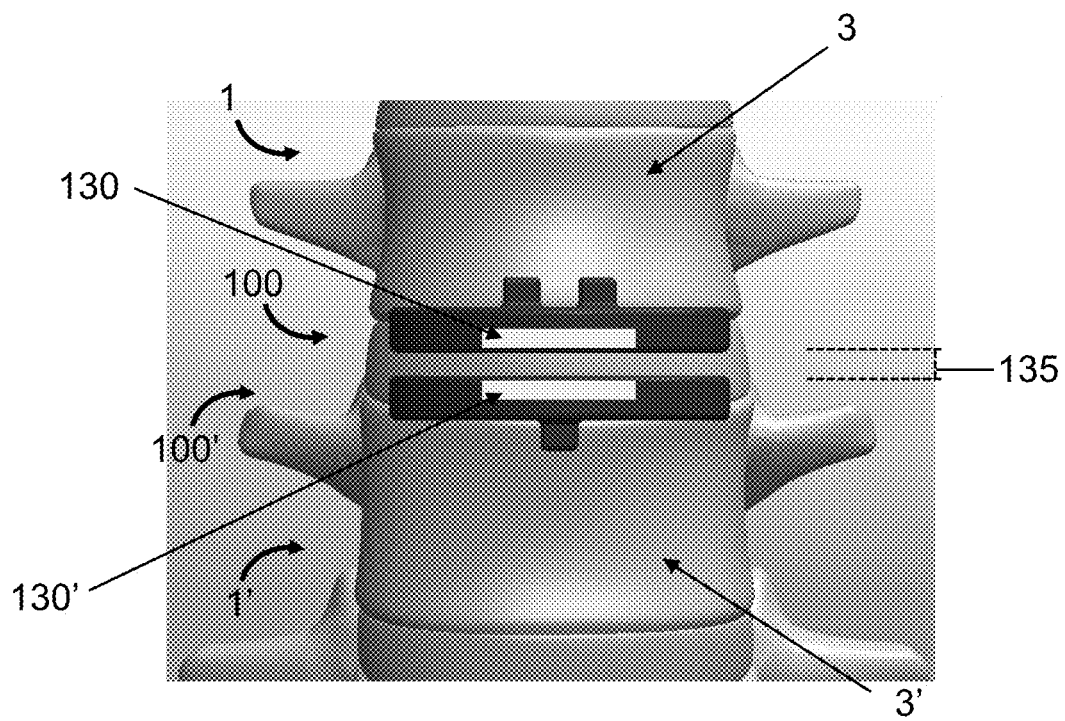

FIGS. 7A and 7B are different views of a two-plate non-contacting intervertebral disc replacement device according to embodiments of the present invention, implanted into a motion segment of a human spine, in which the magnet of the superior plate and the magnet of the inferior plate are shown. FIG. 7A is lateral view of the device implanted into the motion segment, and FIG. 7B is an anterior view of the device implanted into the motion segment.

Figure 8A:
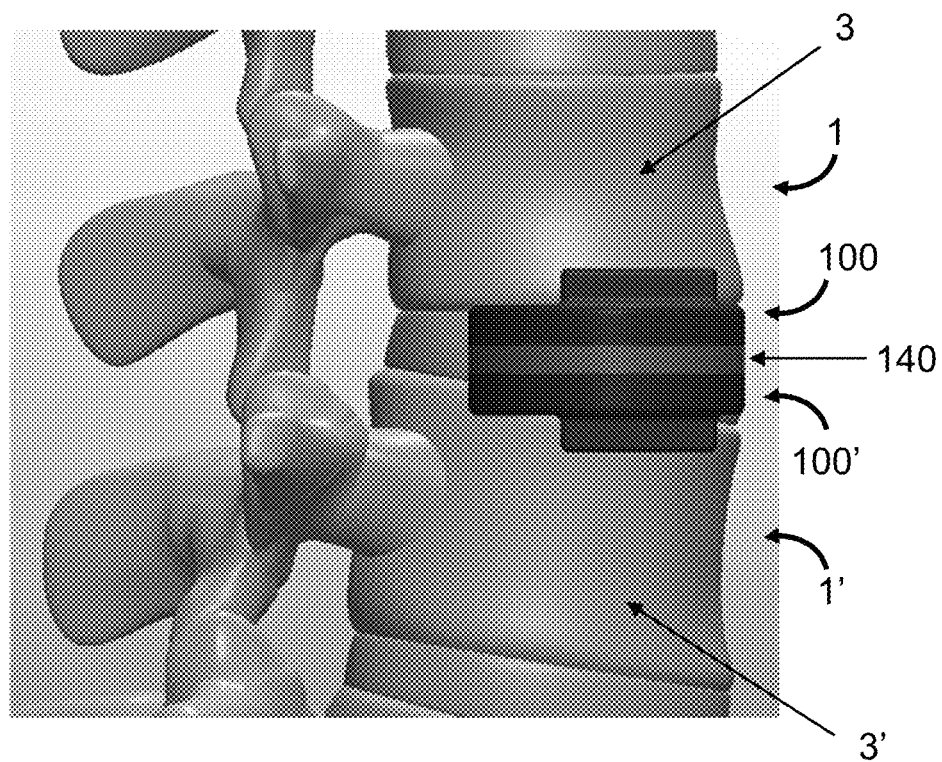
Figure 8B:
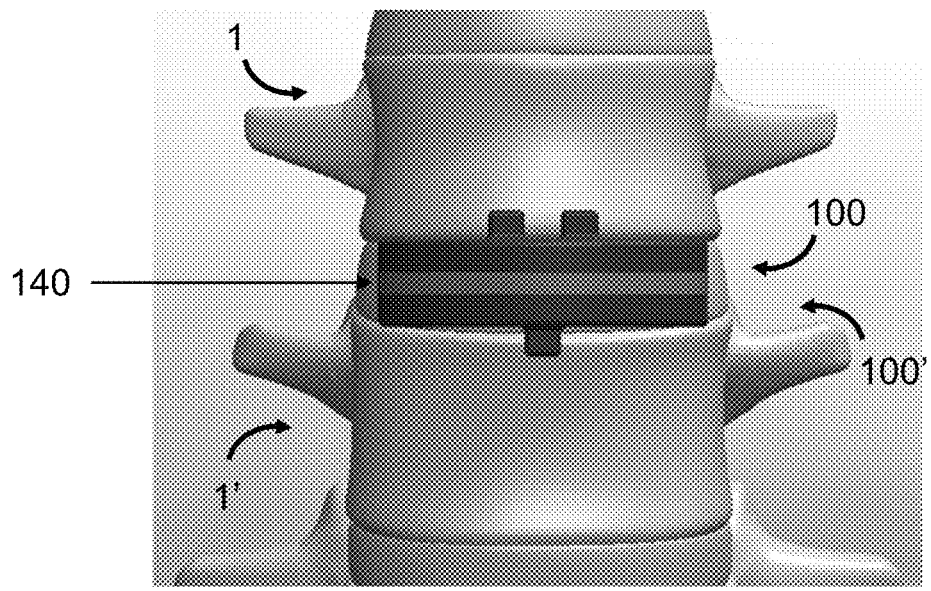

FIGS. 8A and 8B are different views of a two-plate non-contacting intervertebral disc replacement device according to embodiments of the present invention, implanted into a motion segment of a human spine, in which the device includes a linking material between each plate.

FIG. 8A is lateral view of the device implanted into the motion segment, and FIG. 8B is an anterior view of the device implanted into the motion segment.

Figure 9A:
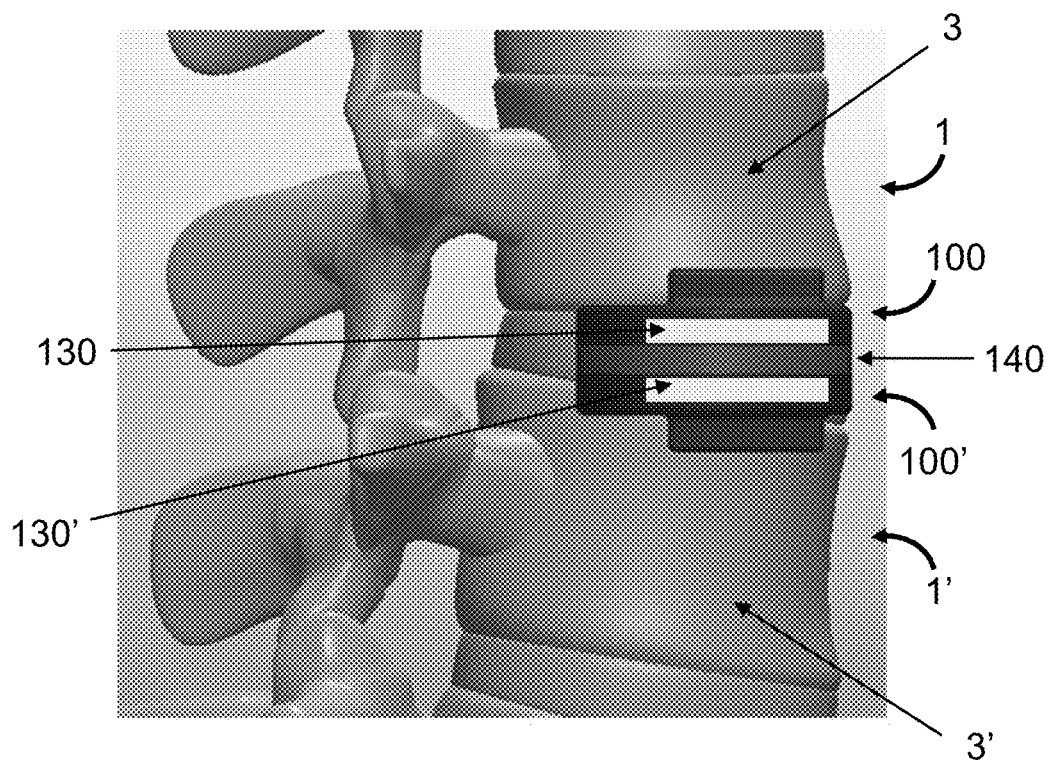
Figure 9B:
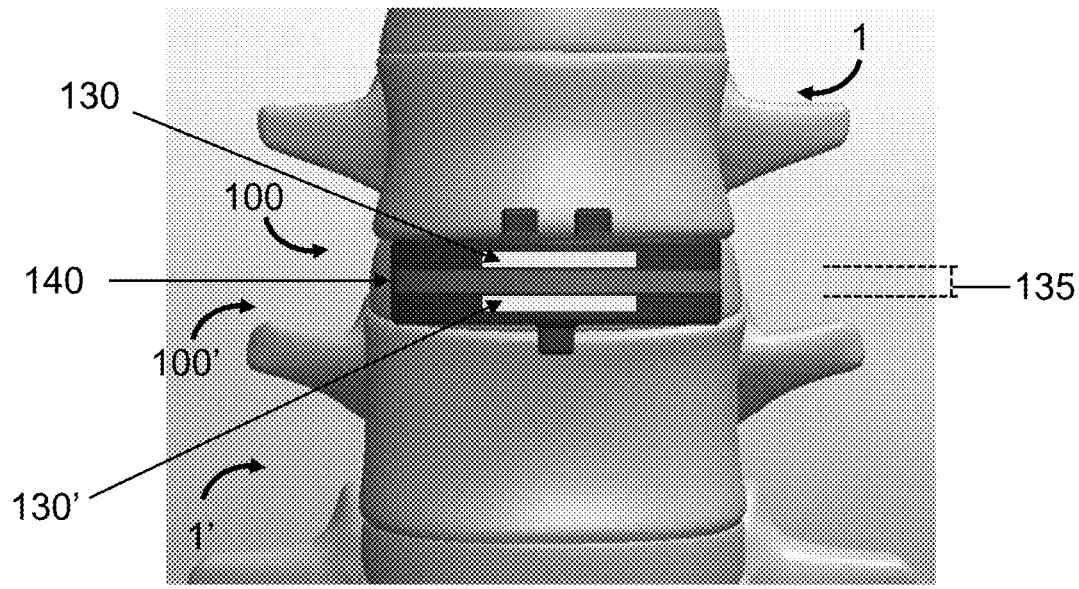

FIGS. 9A and 9B are different views of a two-plate non-contacting intervertebral disc replacement device according to embodiments of the present invention, implanted into a motion segment of the human spine, in which the device includes a material between each plate and the magnet of a superior plate and the magnet of the inferior plate are shown. FIG. 9A is lateral view of the device implanted into the motion segment, and FIG. 9B is an anterior view of the device implanted into the motion segment.

Figure 10A:
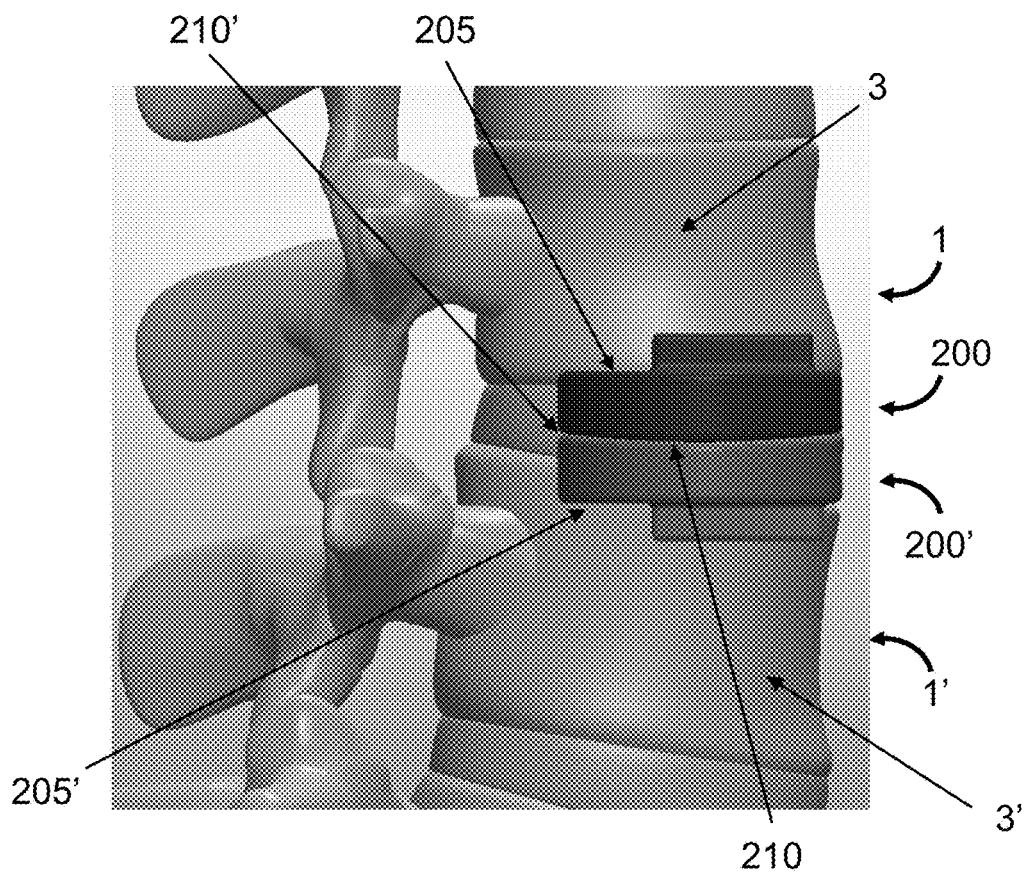
Figure 10B:
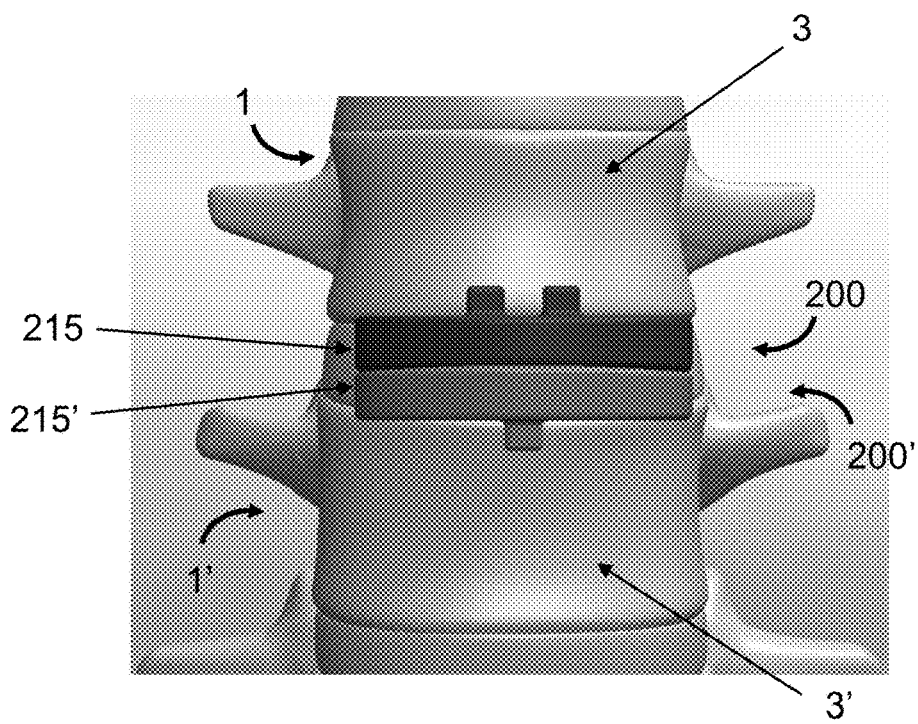

FIGS. 10A and 10B are different views of a two-plate contacting intervertebral disc replacement device according to embodiments of the present invention, implanted into a motion segment of a human spine. FIG. 10A is lateral view of the device implanted into the motion segment, and FIG. 10B is an anterior view of the device implanted into the motion segment.

Figure 11A:
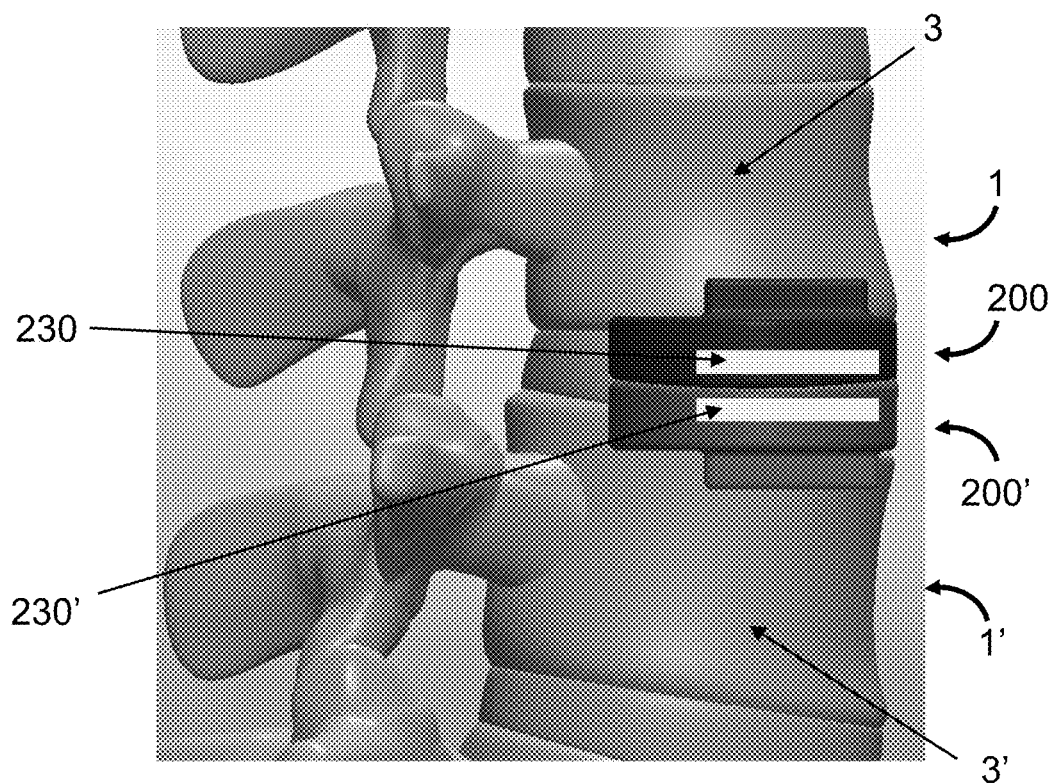
Figure 11B:
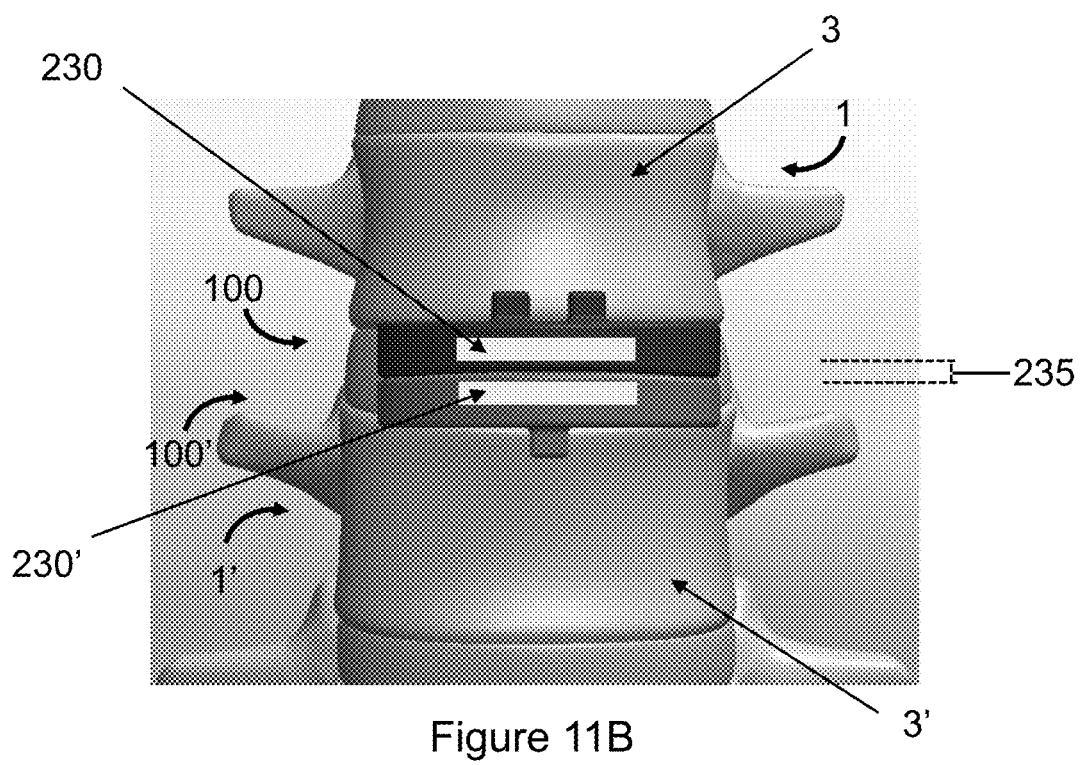

FIGS. 11A and 11B are different views of a two-plate contacting intervertebral disc replacement device according to embodiments of the present invention, implanted into a motion segment of a human spine, in which the magnet of the superior plate and the magnet of the inferior plate are shown. FIG. 11A is lateral view of the device implanted into the motion segment, and FIG. 11B is an anterior view of the device implanted into the motion segment.

Figure 12A:
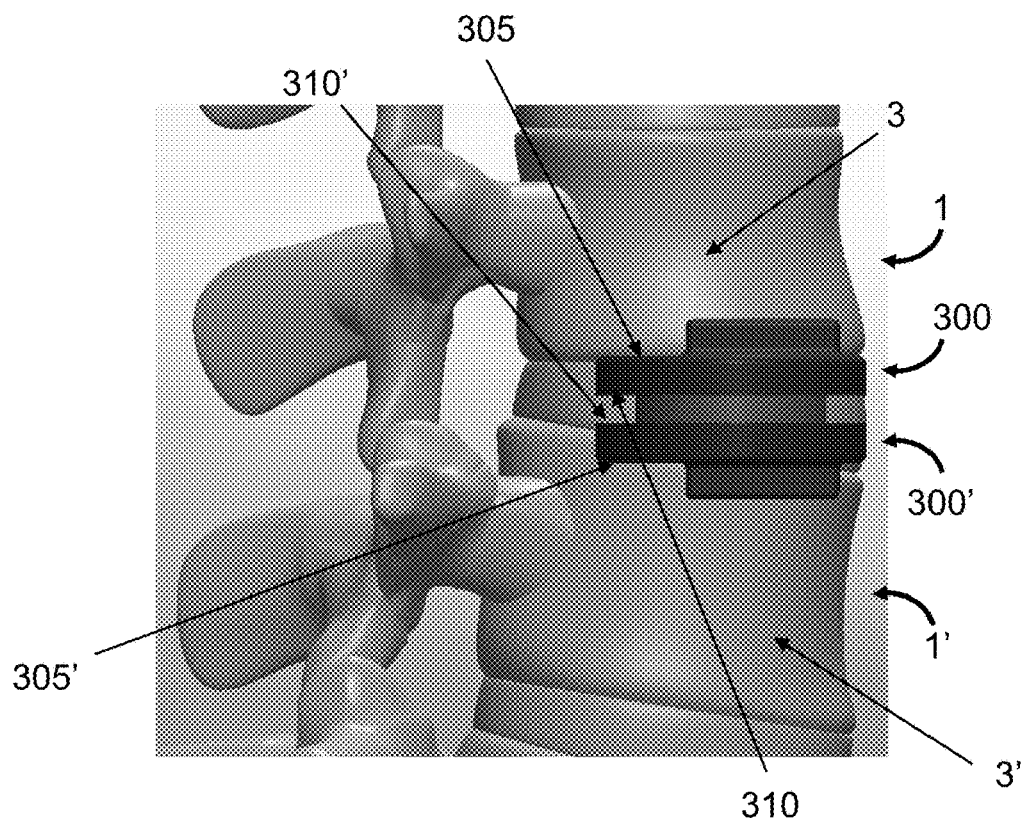
Figure 12B:
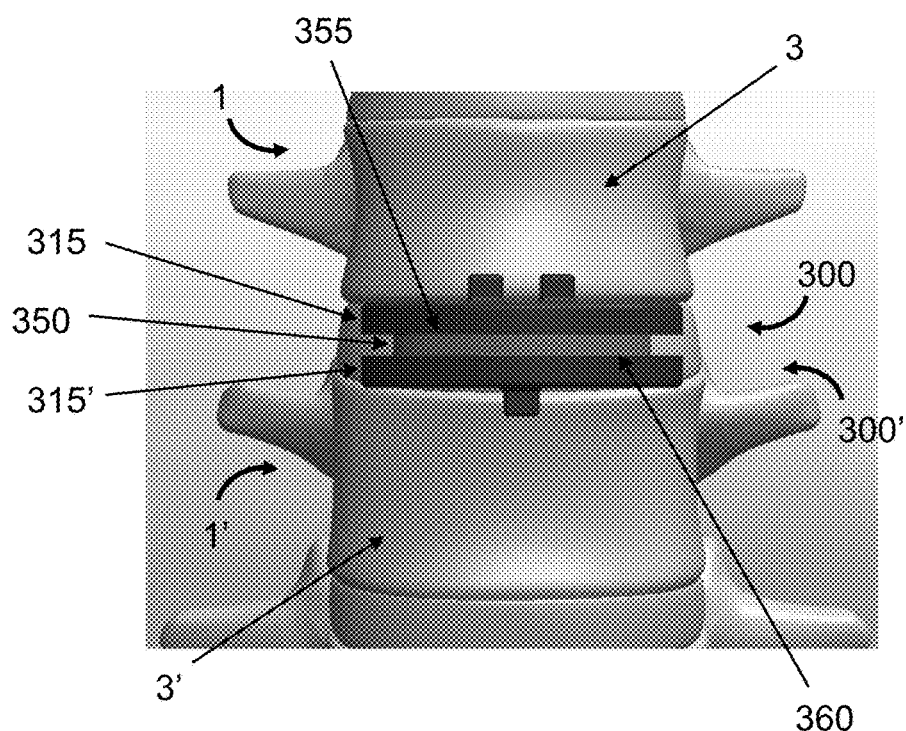

FIGS. 12A and 12B are different views of a two-plate-with-spacer contacting intervertebral disc replacement device according to embodiments of the present invention, implanted into a motion segment of the human spine. FIG. 12A is lateral view of the device implanted into the motion segment, and FIG. 12B is an anterior view of the device implanted into the motion segment.

Figure 13A:
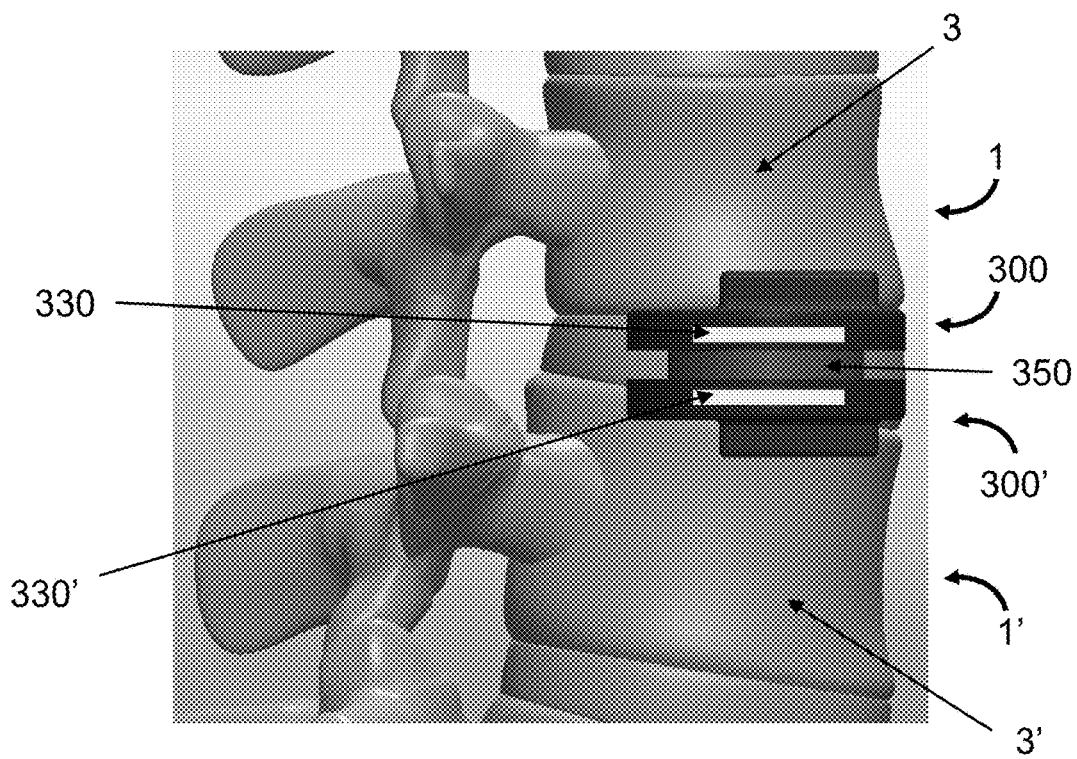
Figure 13B:
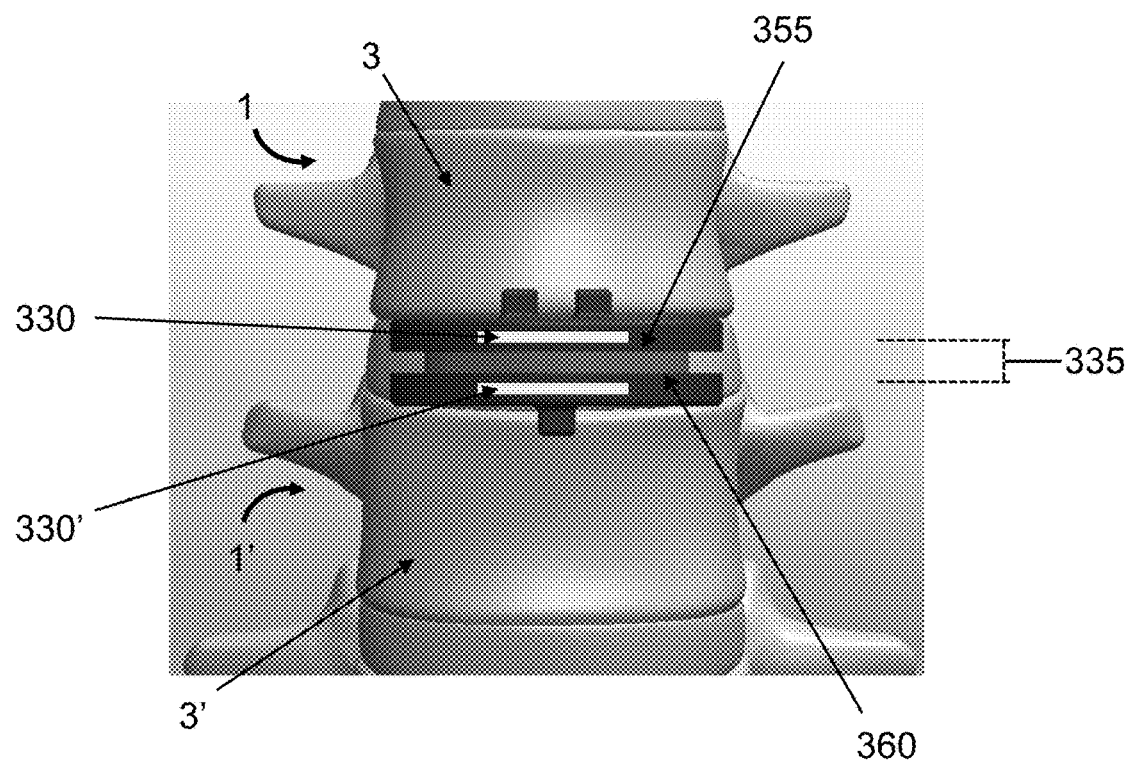

FIGS. 13A and 13B are different views of a two-plate-with-spacer contacting intervertebral disc replacement device according to embodiments of the present invention, implanted into a motion segment of the human spine, in which the magnet of the superior plate and the magnet of the inferior plate are shown. FIG. 13A is lateral view of the device implanted into the motion segment, and FIG. 13B is an anterior view of the device implanted into the motion segment.

Figure 14A:
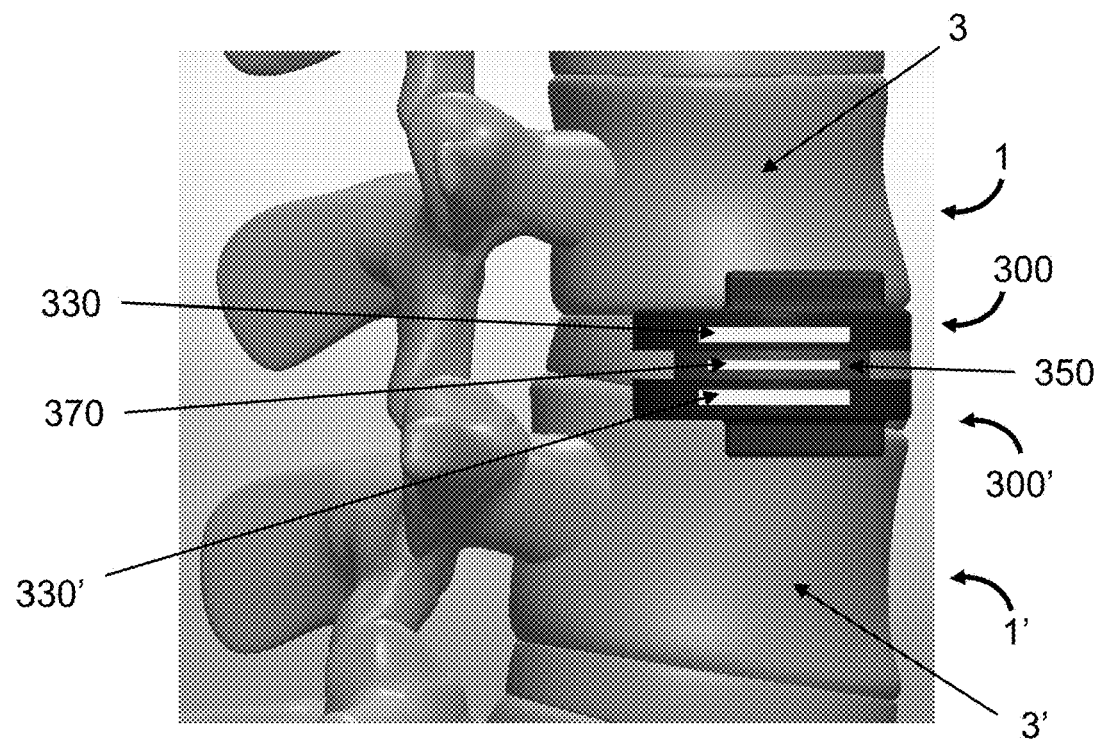
Figure 14B:
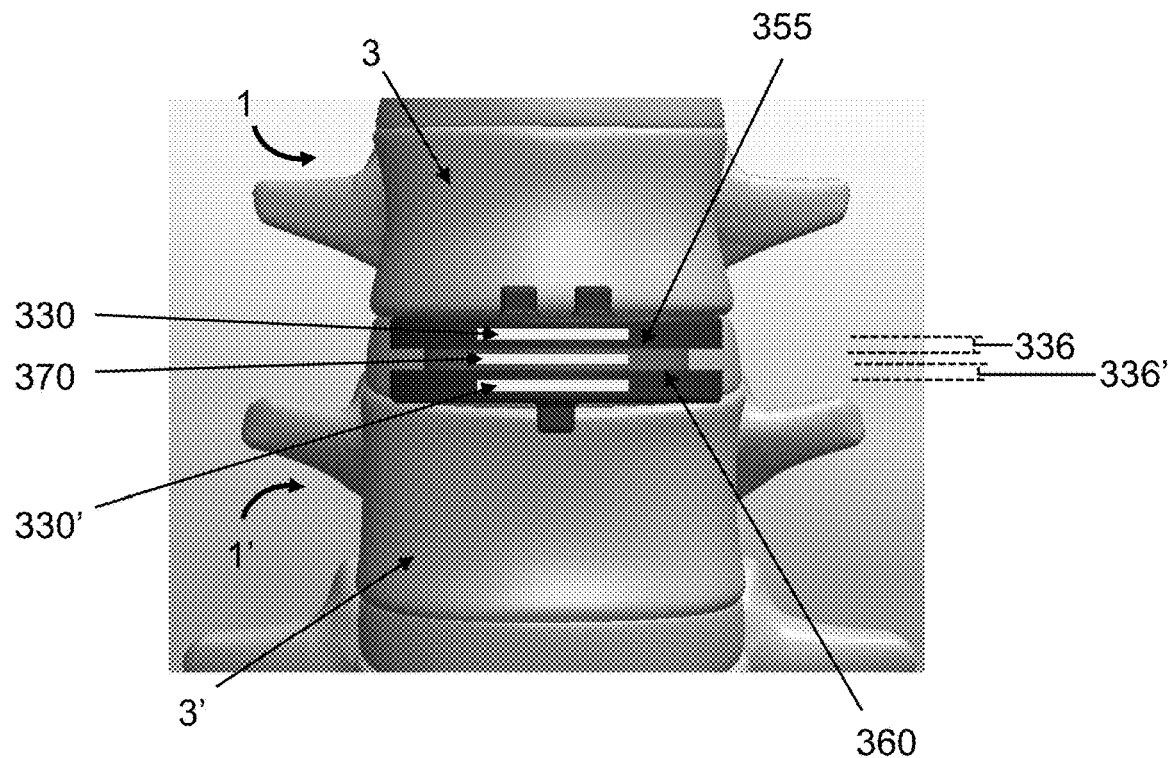

FIGS. 14A and 14B are different views of a two-plate-with-spacer contacting intervertebral disc replacement device according to embodiments of the present invention, implanted into a motion segment of the human spine, in which the magnet of the superior plate, the magnet of the inferior plate, and the magnet of the spacer are shown. FIG. 14A is lateral view of the device implanted into the motion segment, and FIG. 14B is an anterior view of the device implanted into the motion segment.

Figure 15A:
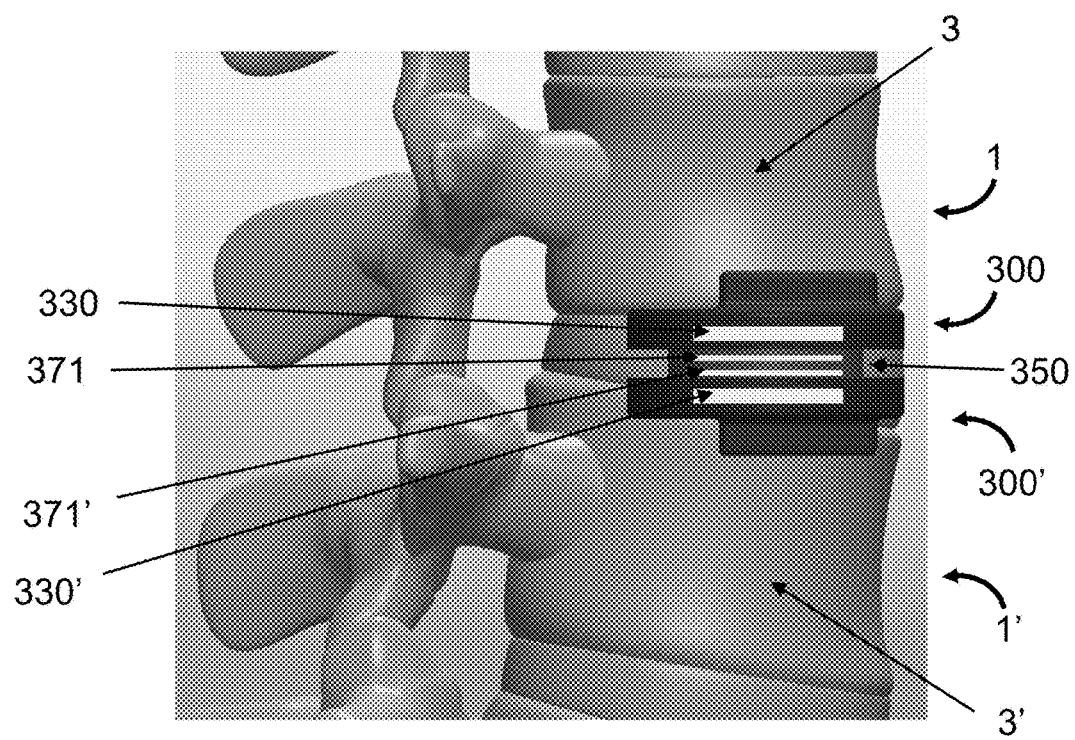
Figure 15B:
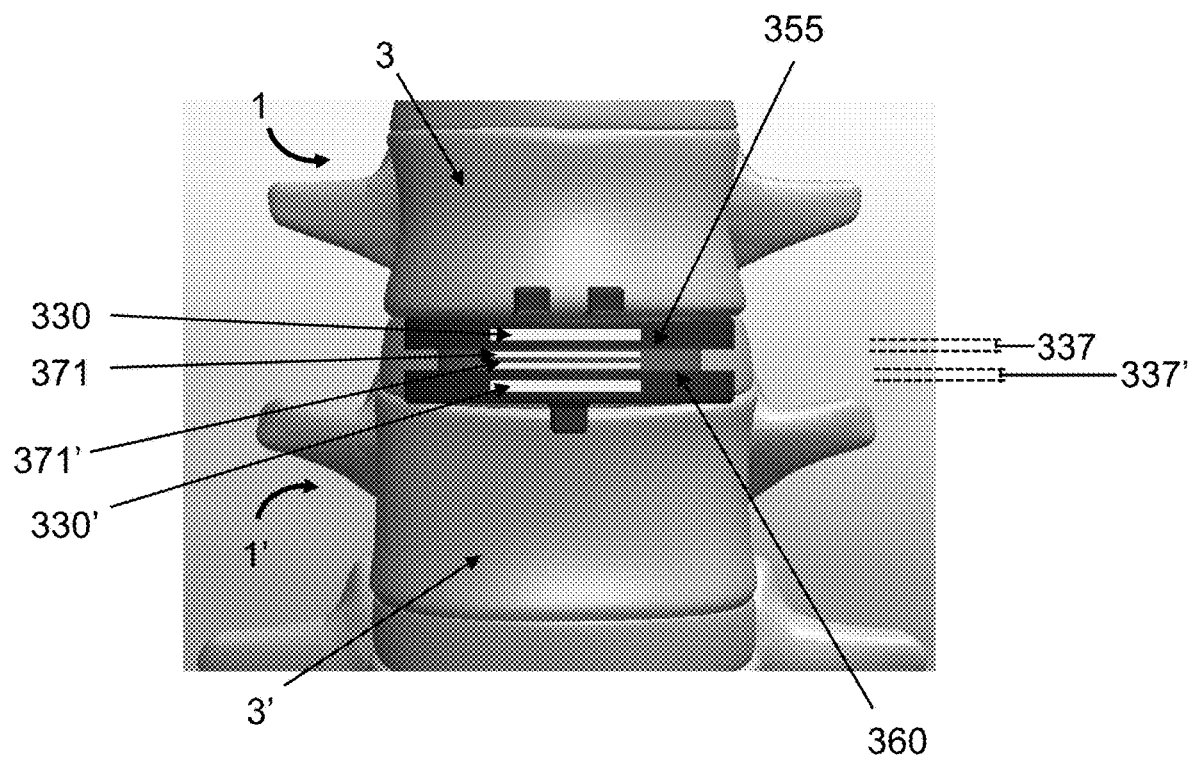

FIGS. 15A and 15B are different views of a two-plate-with-spacer contacting intervertebral disc replacement device according to embodiments of the present invention, implanted into a motion segment of the human spine, in which the magnet of the superior plate, the magnet of the inferior plate, and the magnets of the spacer that are in association with each articulating surface of the spacer are shown. FIG. 15A is lateral view of the device implanted into the motion segment, and FIG. 15B is an anterior view of the device implanted into the motion segment.

Figure 16:
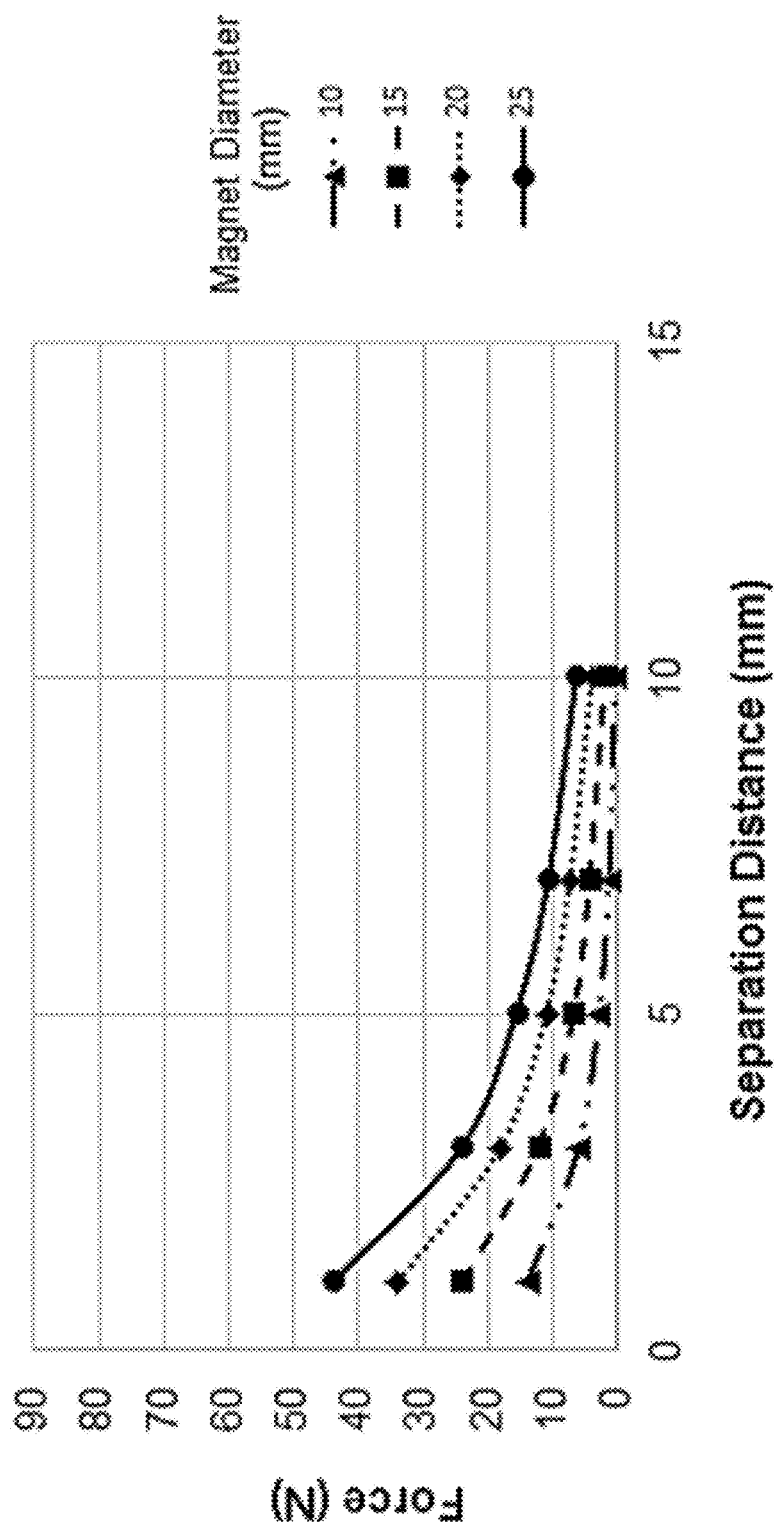

FIG. 16 is a plot of the repulsion forces generated between the magnets of the disc replacement devices according to embodiments of the present invention at various magnet diameters and separation distances, and with a magnet thickness of 3 mm, as set forth in Example 1.

Figure 17:
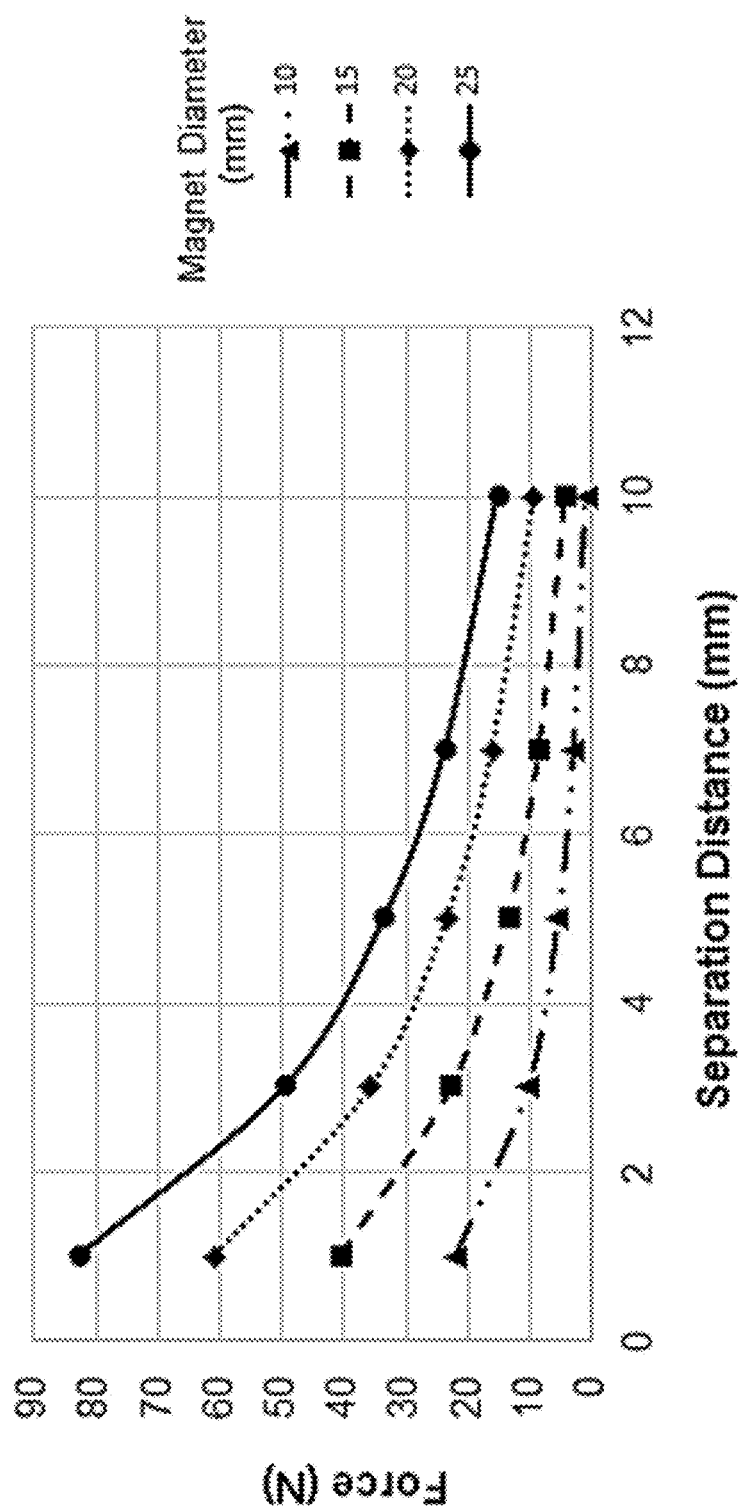

FIG. 17 is a plot of the repulsion forces generated between the magnets of the disc replacement devices according to embodiments of the present invention at various magnet diameters and separation distances, and with a magnet thickness of 5 mm, as set forth in Example 1.

Figure 18:
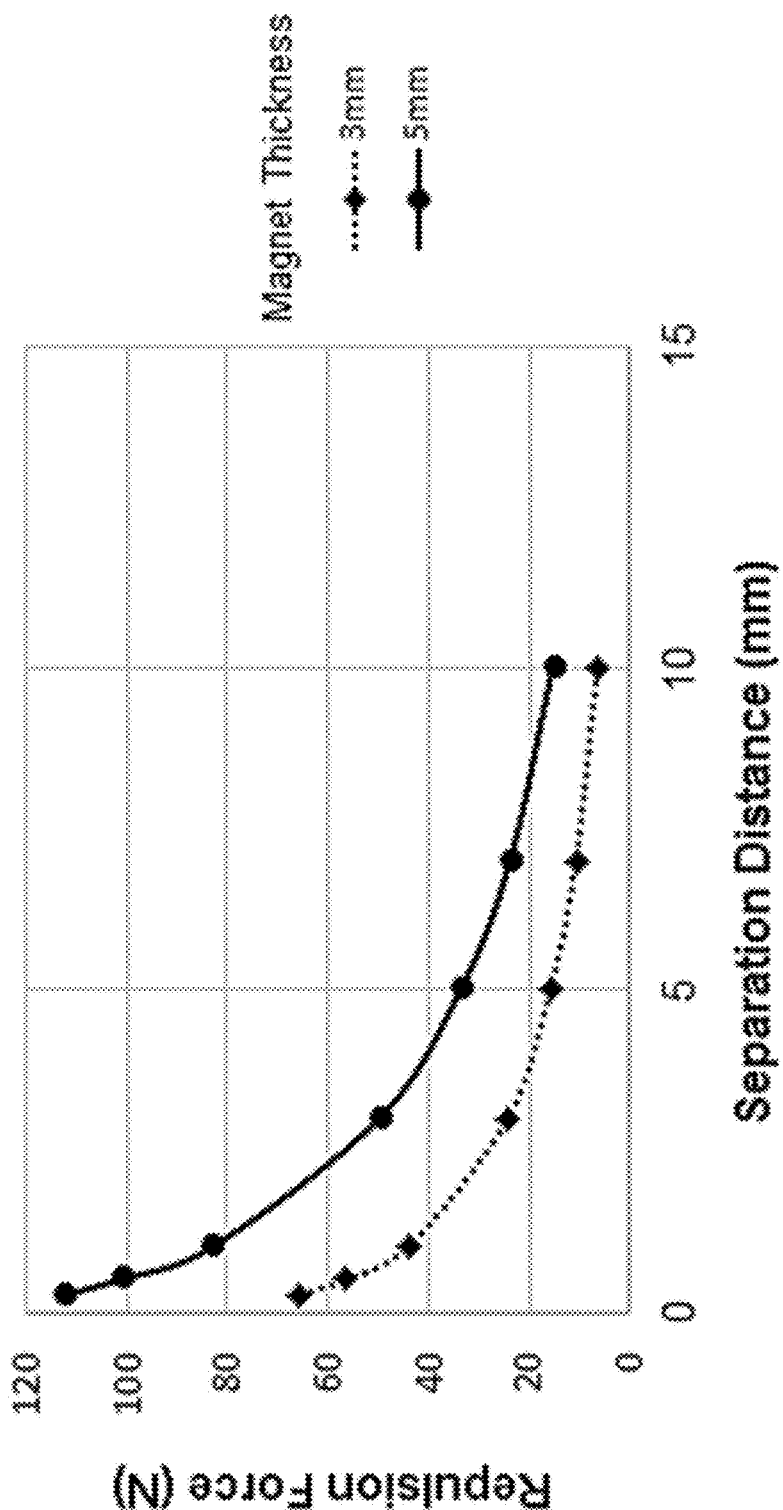

FIG. 18 is a plot of the repulsion forces generated between the magnets of the disc replacement devices according to embodiments of the present invention at various magnet thicknesses and separation distances, and with a magnet diameter of 25 mm, as set forth in Example 1.

Figure 19:
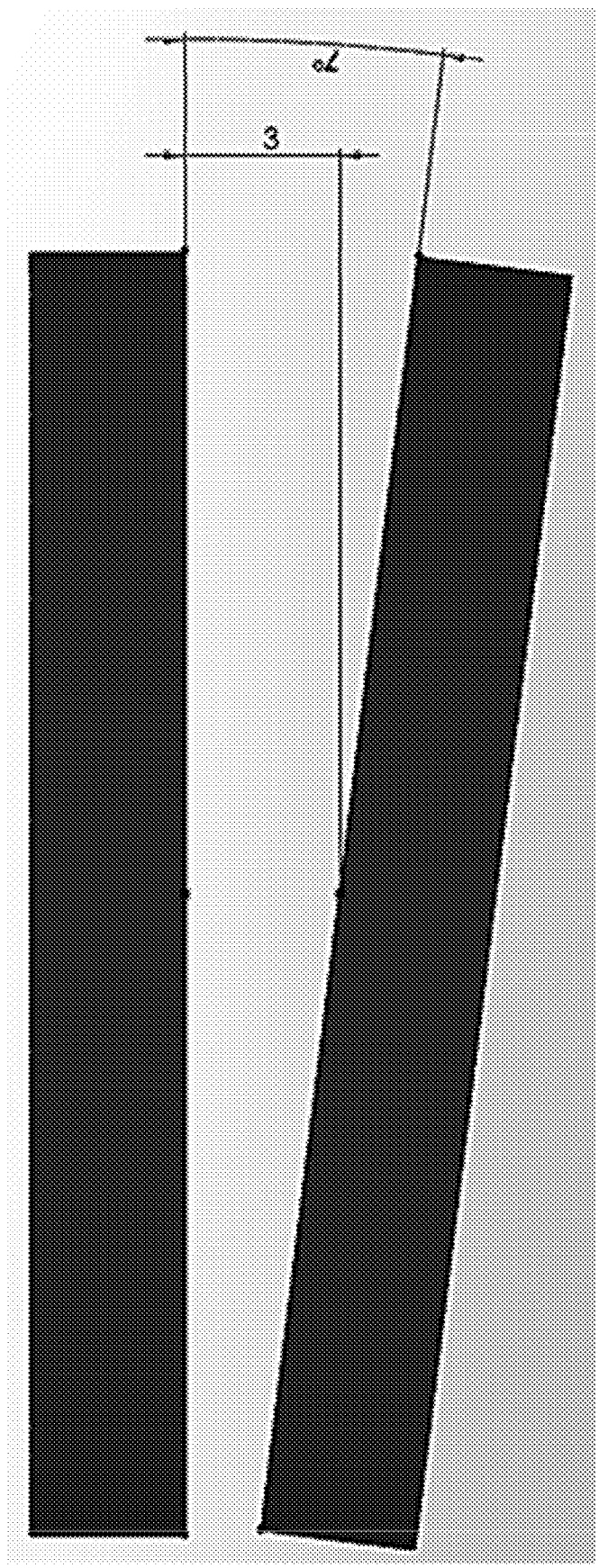

FIG. 19 shows the angle of the magnets of a two-plate non-contact intervertebral disc replacement device according to embodiments of the present invention, as analyzed in Example 2.

Figure 20:
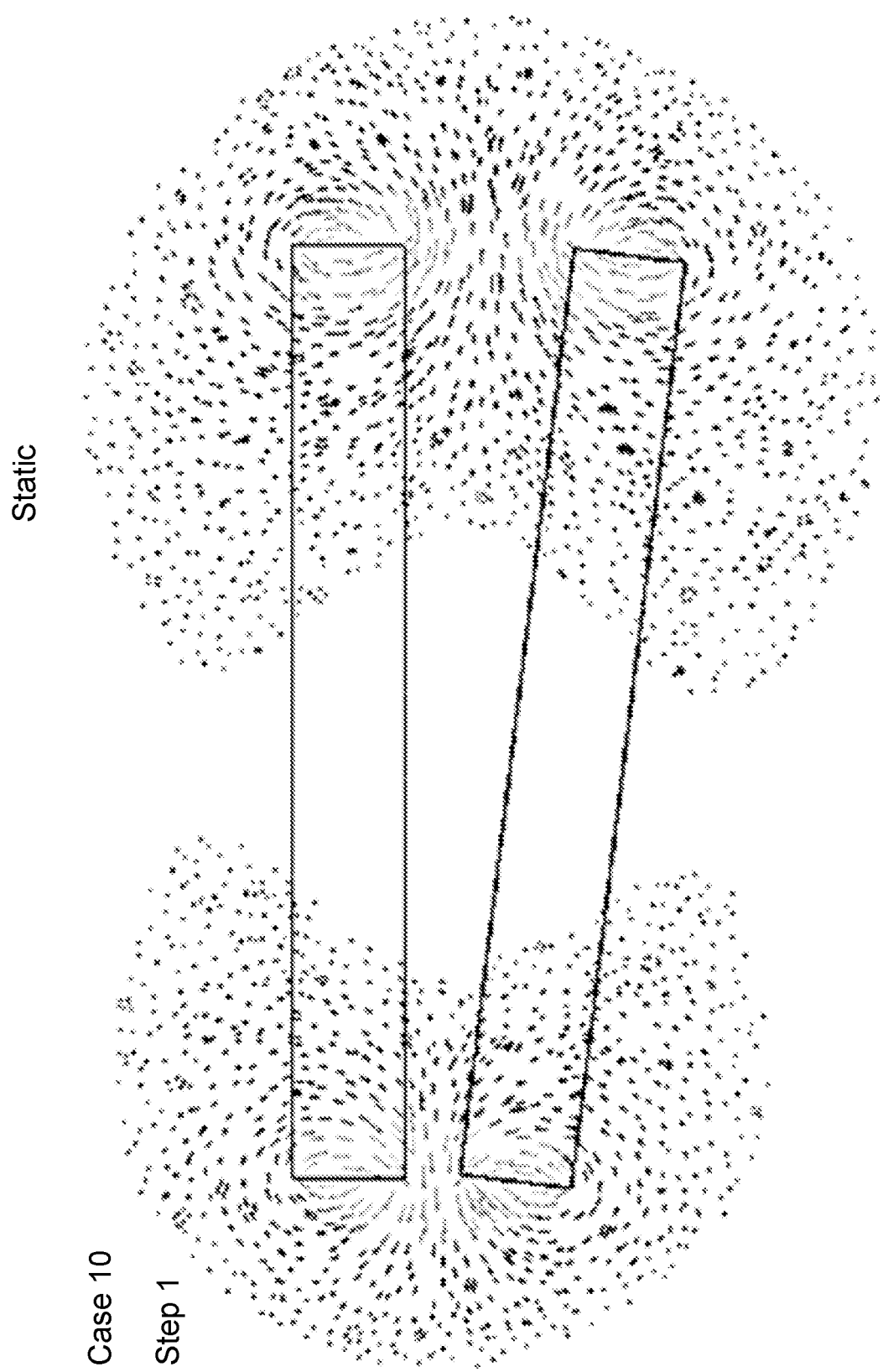

FIG. 20 shows the magnetic fields generated from the magnets of a two-plate non-contact intervertebral disc replacement device according to embodiments of the present invention, as analyzed in Example 2.

DETAILED DESCRIPTION OF THE INVENTION

The present invention relates to intervertebral disc replacement devices and methods thereof. The intervertebral disc replacement device of the present invention comprises magnets, which, upon implantation, generate a magnetic force field to maintain and/or control separation of the two vertebral bodies adjacent to the disc that is being replaced. The separation distance allows a normal range—or at least a desired range—of motion in all planes.

Two-Plate Non-Contacting Intervertebral Disc Replacement Device

An aspect of the invention relates to an intervertebral disc replacement device that comprises a superior plate and an inferior plate, in which each plate contains one or more magnets embedded therein. Upon implantation, the superior plate is fixated to the adjacent vertebra superior to the disc that is being replaced, the inferior plate is fixated to the adjacent vertebra inferior to the disc that is being replaced, and the superior plate and inferior plate are separated by a distance from each other, and thus there is no contact. The terms "superior" and "inferior" reflect how these plates are positioned relative to each other when the device is implanted as a disc replacement.

Without being bound by theory, a benefit of the two-plate non-contacting device compared to all other disc replacements is that there is no wear and no wear debris generated by the plates. Such a result occurs, because the plates do not have any contacting surfaces, or at least the contacting surfaces are reduced. Wear debris can and often does have serious detrimental effects on the tissues surrounding any articulating joint replacement and may be a major factor in failure and need for revision of the device. This is primarily due to the adverse tissue reaction that wear debris particles can elicit as a result of their size and composition.

An example of a two-plate non-contacting intervertebral disc replacement device according to embodiments of the invention is shown in FIGS. 2A-3B. Superior plate 100 and inferior plate 100' may each comprise a fixation surface 105 and 105', respectively; an inner surface 110 and 110', respectively; and an edge surface 115 and 115', respectively. In embodiments of the invention, upon implantation as shown in FIGS. 6A-9B, fixation surface 105 and 105' may face the endplate of the vertebrae adjacent to the intervertebral disc that is being replaced, such that fixation surface 105 may face the endplate of vertebra 1 that is superior to the disc that is being replaced, and fixation surface 105' may face the endplate of vertebra 1' that is inferior to the intervertebral disc that is being replaced. In addition, inner surface 110 of superior plate 100 may face inner surface 110' of inferior plate 100'. Edge surface 115 and 115' refers to the surface that is formed from the thickness of the plate 100 and 100', respectively.

Each plate may also comprise a fixation extension that extends beyond the fixation surface of the plate. This is illustrated in FIGS. 2A-3B, in which plate 100 and 100' comprises fixation extension 120 and 120'. The fixation extension may comprise a single unit (see, e.g., fixation extension 120' of inferior plate 100' shown in FIG. 2B or 3B) or may comprise more than one unit (see, e.g., fixation extension 120 of superior plate 100 shown in FIG. 2A or 3A). Upon implantation, as shown for example in FIGS. 6A-7B, fixation extension 120 and 120' may be a surface that can adhere to the outside surface of vertebral body 3 and 3', respectively, of vertebra 1 and 1', respectively, that are adjacent to the intervertebral disc being replaced.

Each plate may generally have the same shape, although that shape may vary. The plate may comprise a shape that generally resembles a sphere, cylinder, ellipsoid, prism (e.g., cube, rectangular prism, triangular prism, pentagonal prism, hexagonal prism, etc.), pyramid, cone, or other three-dimensional shapes known in the art. In some embodiments, the plates may comprise a cross-sectional shape that generally resembles the cross-sectional shape of the vertebral body portion of a vertebra.

In some embodiments, the plates may comprise a shape that resembles, is derived from, or is largely the same as, plates that are apart of intervertebral disc replacement devices known in the art. Such devices include those that are described in U.S. Pat. Nos. 6,001,130, 7,491,240, 7,494,508, 7,766,966, 8,353,964, 8,858,635, 8,911,498, 9,566,164, and 9,883,945, each of which are incorporated herein by reference.

The fixation surface and inner surface of each plate (i) may be flat as shown in FIGS. 2A-3B (see fixation surface 105 and 105' and inner surface 110 and 110'); (ii) may be curved (not shown); or (iii) a combination thereof (e.g., some portions of the surfaces are flat, while other portions are curved) (not shown). A curvature may be present on the inner surface of one or both plate as needed to provide the desired distances for separation between the plates, and/or to prevent contact between the inner surface of the superior plate and the inner surface f inferior plate at potential extreme angles of motion or translation.

The fixation surface of the plates may comprise a surface geometry, a surface feature, or a combination thereof, that can help adhere the plates to the endplates of the vertebrae adjacent to the intervertebral disc that is being replaced. The surface geometry and/or surface feature may also provide initial stability and resistance to torsional or shear loading to the plates. A surface geometry for the present invention may include, but is not limited to, a texture, porous coating, bioactive coating, and a combination thereof. A surface feature for the present invention may include, but is not limited to, one or more keels, one or more pegs, one or more screws, and the like, including a combination thereof.

The inner surface of the plates may be polished or may have an as-fabricated surface. In some embodiments, the inner surface may have a surface geometry and/or surface feature as described above.

The diameter or, in the case of a non-circular plate, long axis (widest distance across) of the plates (shown as 125 and 125' of plate 100 and 100', respectively, in FIGS. 2A-3B) may be about 3 mm to about 50 mm, or about 5 mm to about 30 mm, or about 10 mm to about 20 mm. The thickness of the plates (shown as 126 and 126' of plate 100 and 100', respectively, in FIGS. 2A-3B) may be about 1 mm to about 15 mm, or about 2 mm to about 10 mm, or about 4 mm to about 8 mm. The fixation extensions may extend beyond the fixation surface by a distance (shown as 127 and 127' of plate 100 and 100', respectively, in FIGS. 2A-3B) of about 0.5 to 5 mm, or about 1 to about 3 mm.

The plates may be of a material appropriate for implantation into the body. For instance, the material may be a metal such as titanium or cobalt chromium alloys; a biopolymer such as PEEK; a ceramic such as aluminum oxide or zirconia alloys; or a combination thereof.

Figure 1A:
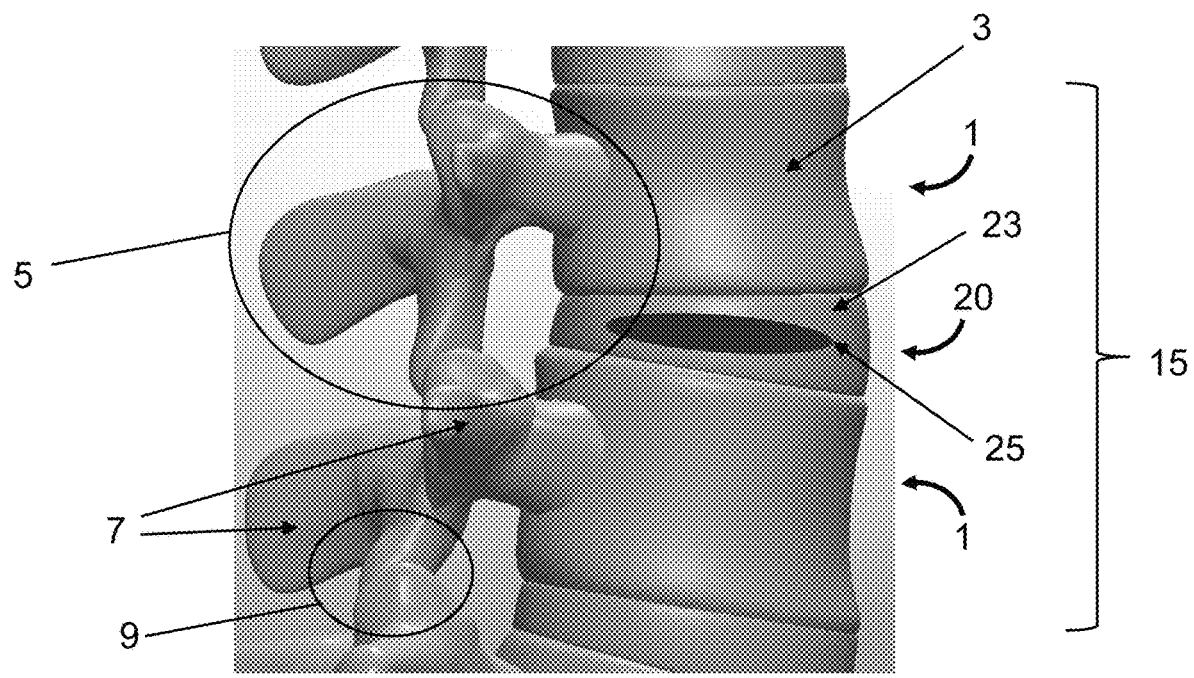
FIGS. 1A and 1B are different views of a motion segment of the human spine.
Figure 1B:
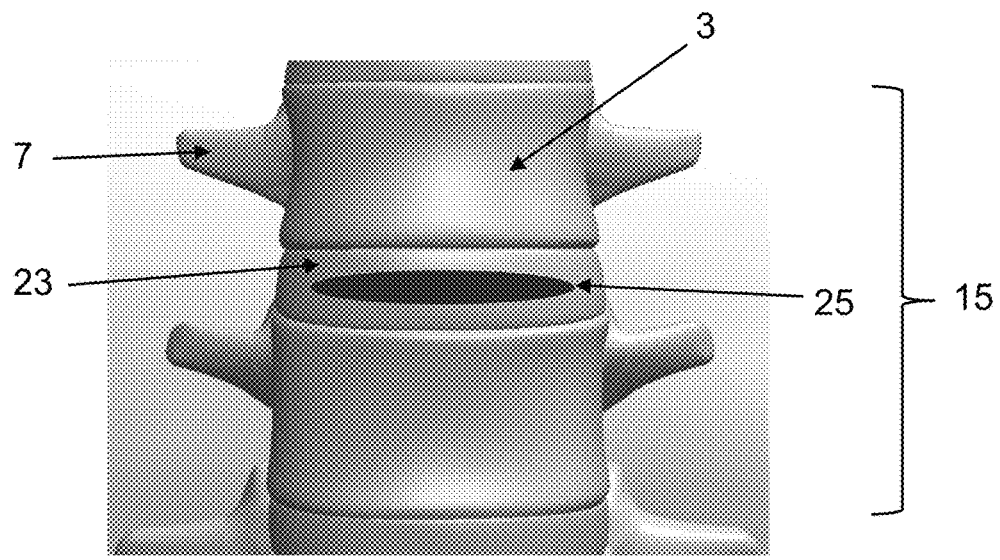
Figure 2A:
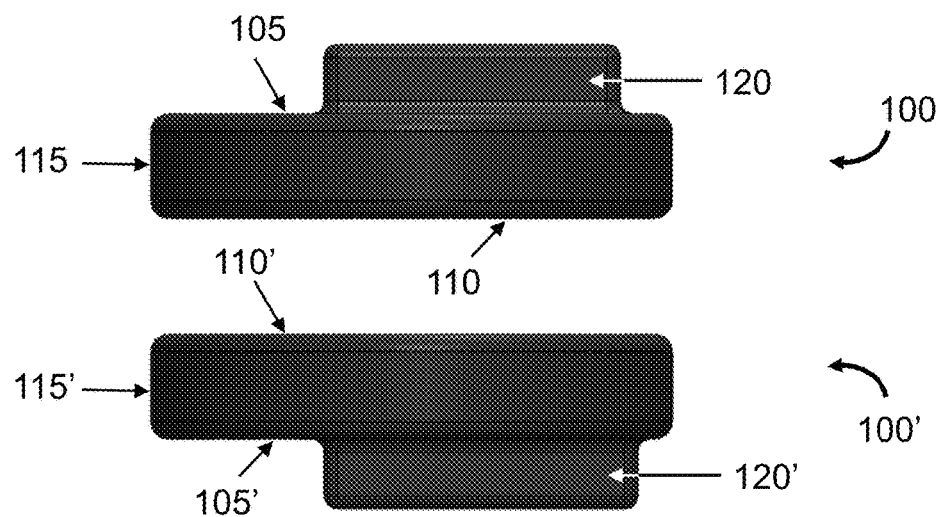
FIGS. 2A and 2B are different views of a two-plate non-contacting intervertebral disc replacement device according to embodiments of the present invention.
Figure 2B:
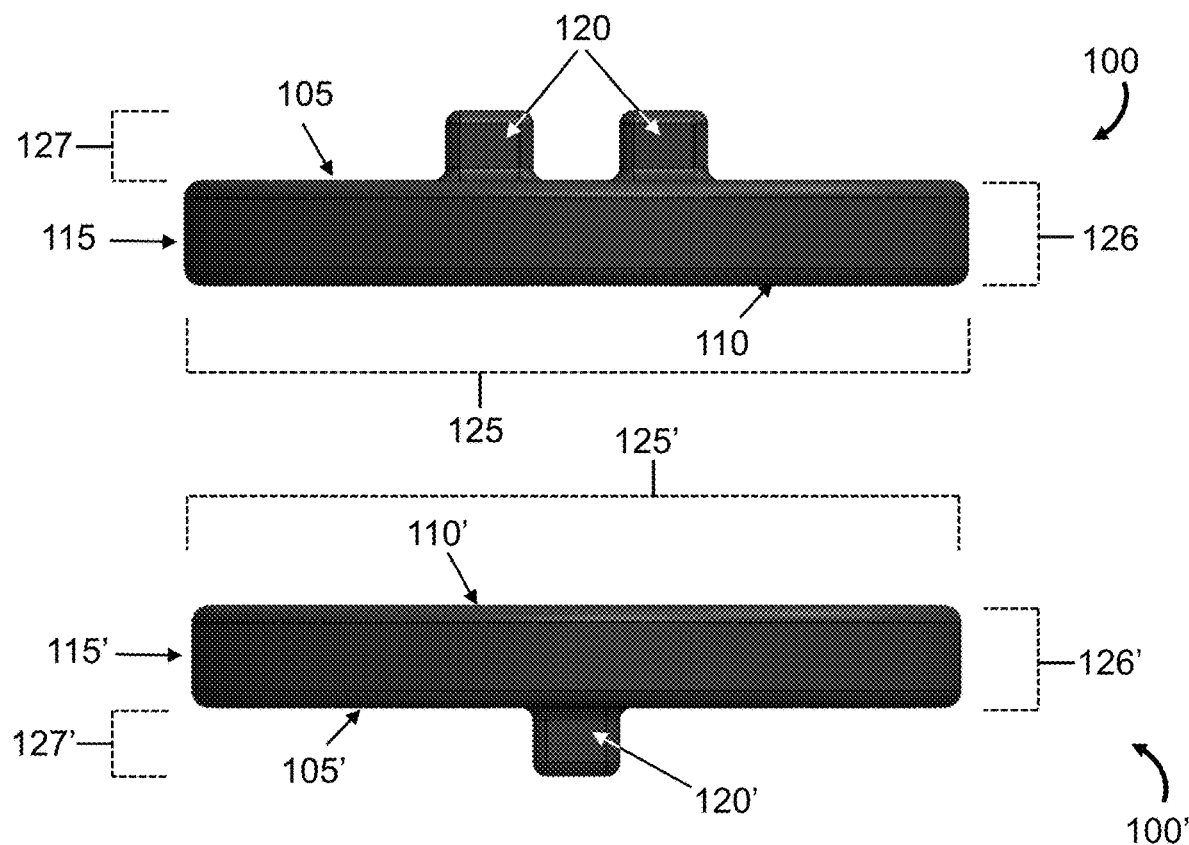
Figure 3A:
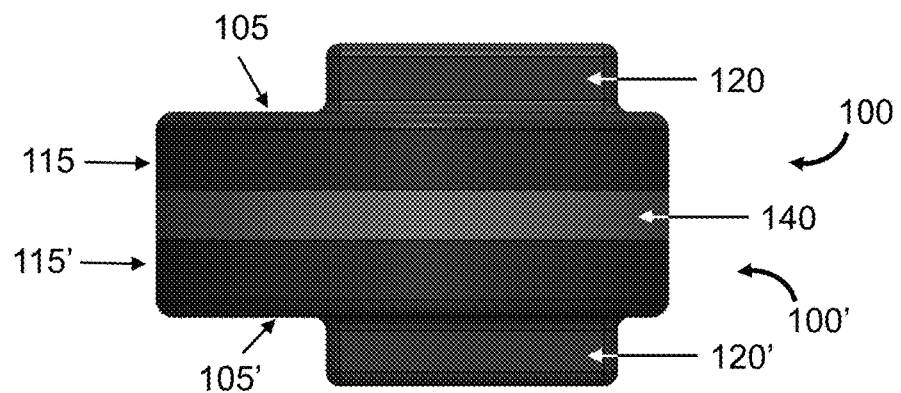
FIGS. 3A and 3B are different views of a two-plate non-contacting intervertebral disc replacement device according to embodiments of the present invention, in which the device includes a linking material between each plate.
Figure 3B:
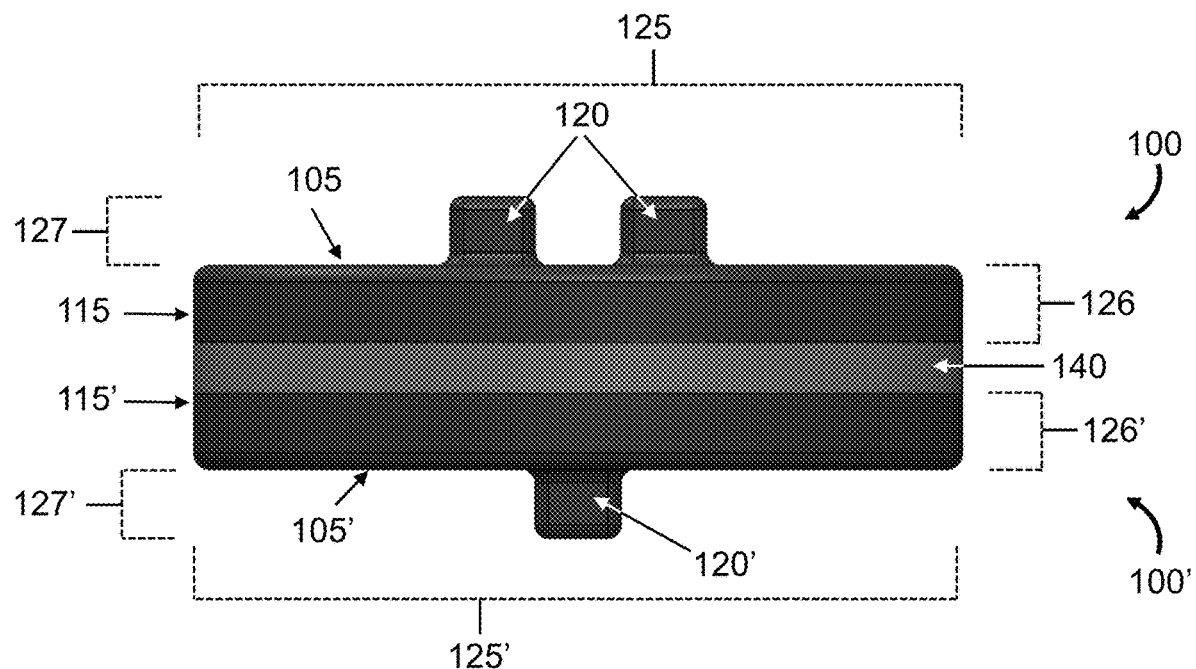

In some embodiments, a linking material may be attached to both the superior and inferior plates. The material may be between each plate, may cover each plate or a portion of each plate, or both. In some embodiments, the material may be between each plate, such as attached to the inner surface of each plate. An example is shown in FIGS. 3A and 3B, which shows a superior plate 100 and an inferior plate 100', in which a linking material 140 is located between—and attached to—each plate 100 and 100'. The material 140 may be a mesh or similar fabric or a soft material, such as a polyurethane or other polymeric or rubber material. The material may allow the device to be implanted as one piece.

Each plate comprises one or more appropriate-sized rare earth magnets. The one or more magnets may be embedded within the plates, such that the magnet(s) are not exposed to outside of the plate.

The shape of the magnets includes, but is not limited to, a shape that generally resembles a sphere, cylinder, hollow cylinder, ellipsoid, prism (e.g., cube, rectangular prism, triangular prism, pentagonal prism, hexagonal prism, etc.), hollow prism, pyramid, cone, torus, or other three-dimensional shapes known in the art. In some embodiments, more than one magnet may be present in a plate, such as in a configuration or array that provides the appropriate magnetic field for interacting with the magnet(s) of the other plate. If more than one magnet is present, the magnets may have any of the shapes described above, or portions thereof.

The magnets may comprise materials known in the art. For example, the magnets may be iron-based, nickel-based, cobalt-based, or an alloy of rare-earth metals. In certain embodiments, the magnets may be a rare-earth magnet, which generally has strong attraction and repulsion forces and have high retentive capacity and resistance to demagnification. In a preferred embodiment, the rare-earth magnet is an alloy of neodymium, iron, and boron ("NdFeB"). NdFeB magnets provide strong permanent magnetism, high retentive capacity, and resistance to demagnetization.

The diameter or, in the case of a non-circular magnet, long axis (widest distance across) of the magnet(s) may be about 5 mm to about 30 mm, or about 10 mm to about 20 mm. The thickness of the magnet(s) plate may be about 0.5 mm to about 10 mm, or about 1 mm to about 6 mm.

One of ordinary skill in the art would be able to determine the arrangement of magnet(s) in the superior plate and magnet(s) in the inferior plate in order to achieve a prescribed magnetic force between the magnet(s) of the superior plate and the magnet(s) of the inferior plate, based upon the teachings in the Examples provided below. For example, the skilled artisan would understand from Example 1 the factors that impact the generated magnetic force, including magnet thickness, the magnet diameter, and the separation distance between the magnets, and understand the size of the magnets and arrangement of the magnets within the superior and inferior plates necessary to apply the prescribed force. Thus, the skilled artisan can determine how to arrange the magnets by considering the size and dimensions of the space of the disc that requires replacement, the type of force that is required for the treatment (e.g., a levitating force or a reducing force to decrease wear), as well as other factors such as the subject's weight, height, activity level, etc., which could all have an effect on loading forces experienced in the spine.

Two-Plate Contacting Intervertebral Disc Replacement Device

An aspect of the invention relates to an intervertebral disc replacement device that comprises a superior plate and an inferior plate, in which each plate contains one or more magnets embedded therein. Upon implantation, the superior plate is fixated to the adjacent vertebra superior to the disc that is being replaced, the inferior plate is fixated to the adjacent vertebra inferior to the disc that is being replaced, and the superior plate and the inferior plate are in contact with each other via articulating surfaces.

Without being bound by theory, an advantage of a two-plate contacting device with non-zero loading across the articulating surfaces may be the additional stability provided by the articulating surfaces. Such stability helps produce and maintain normal or desired size and motion, as well as constrain any abnormal motions or translations created by the magnetic fields generated from the embedded magnets or by the body. In addition, the additional stability provided by the two-plate contacting device can help reduce wear and the generation of wear debris. As noted above, wear debris can elicit an adverse tissue reaction which can lead to treatment failure and need for device removal.

Figure 4A:
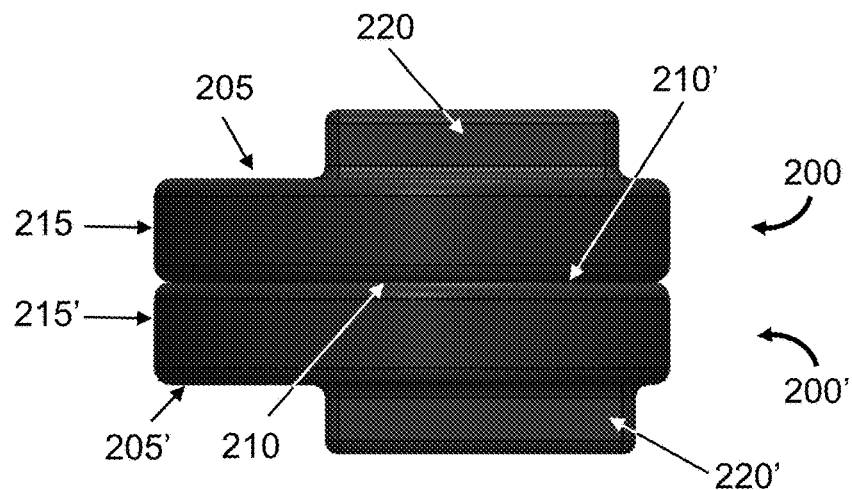
FIGS. 4A and 4B are different views of a two-plate contacting intervertebral disc replacement device according to embodiments of the present invention.
Figure 4B:
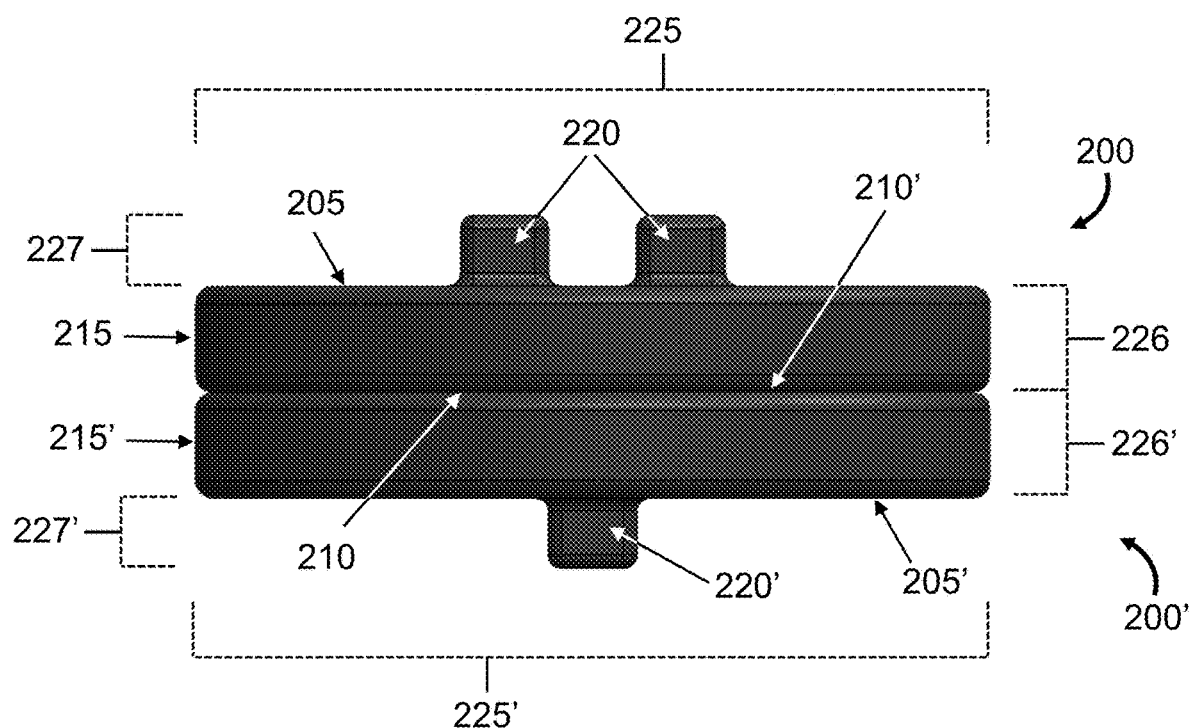

An example of a two-plate contacting intervertebral disc replacement device according to embodiments of the invention is shown in FIGS. 4A and 4B. Superior plate 200 and inferior plate 200' may each comprise a fixation surface 205 and 205', respectively; an articulating surface 210 and 210', respectively; and an edge surface 215 and 215', respectively. In embodiments of the invention, upon implantation as shown in FIGS. 10A-11B, fixation surface 205 and 205' may face the endplate of the vertebrae adjacent to the intervertebral disc that is being replaced, such that fixation surface 205 may face the endplate of vertebra 1 that is superior to the disc that is being replaced, and fixation surface 205' may face the endplate of vertebra 1' that is inferior to the intervertebral disc that is being replaced. Further, articulating surface 210 of the superior plate 200 may articulate against articulating surface 210' of inferior plate 200'. Edge surface 215 and 215' is formed from the thickness of plate 200 and 200', respectively.

Each plate may also comprise a fixation extension that extends beyond the fixation surface of the plate. This is illustrated in FIGS. 4A and 4B, in which plate 200 and 200' comprises fixation extension 220 and 220', respectively. The fixation extension may comprise a single unit (see, e.g., fixation extension 220' of inferior plate 200' shown in FIG. 4B) or may comprise more than one unit (see, e.g., fixation extension 220 of superior plate 200 shown in FIG. 4A). Upon implantation, as shown for example in FIGS. 10A-11B, fixation extension 220 and 220' may be a surface that can adhere to the outside surface of vertebral body 3 and 3', respectively, of vertebra 1 and 1', respectively, that are adjacent to the intervertebral disc being replaced.

Each plate may generally have the same shape, although that shape may vary. The plates may comprise a shape that generally resembles a sphere, cylinder, ellipsoid, prism (e.g., cube, rectangular prism, triangular prism, pentagonal prism, hexagonal prism, etc.), pyramid, cone, or other three-dimensional shapes known in the art. In some embodiments, each plate may comprise a cross-sectional shape that generally resembles the cross-sectional shape of the vertebral body portion of a vertebra.

In some embodiments, the plates may comprise a shape that resembles, is derived from, or is largely the same as, plates that are apart of intervertebral disc replacement devices known in the art. Such devices include those that are described in U.S. Pat. Nos. 6,001,130, 7,491,240, 7,494,508, 7,766,966, 8,353,964, 8,858,635, 8,911,498, 9,566,164, and 9,883,945, each of which are incorporated herein by reference.

The fixation surface of each plate (i) may be flat as shown in FIGS. 4A and 4B (see fixation surface 205 and 205'); (ii) may be curved (not shown); or (ii) a combination thereof (e.g., some portions of the surfaces are flat, while other portions are curved) (not shown). The fixation surface of the plates may comprise a surface geometry, a surface feature, or a combination thereof, that can help adhere the plates to the endplates of the vertebrae adjacent to the intervertebral disc that is being replaced. The surface geometry and/or surface feature may also provide initial stability and resistance to torsional or shear loading to plates. A surface geometry for the present invention may include, but is not limited to, a texture, porous coating, bioactive coating, and a combination thereof. A surface feature for the present invention may include, but is not limited to, one or more keels, one or more pegs, one or more screws, and the like, including a combination thereof.

The articulating surface of the superior plate and the articulating surface of the inferior plate may have conforming or near-conforming geometries to allow motion through articulation of these surfaces. Examples of such conforming or near-conforming geometries include those resembling a ball-and-socket interface; a cup-and-dish interface; a flat-surface interface; toroidal-surface interface such as the surfaces described in U.S. Pat. No. 9,173,748, which is incorporated herein by reference; or the like.

The diameter or, in the case of a non-circular plate, long axis (widest distance across) of the plates (shown as 225 and 225' of plate 200 and 200', respectively, in FIGS. 4A and 4B) may be about 3 mm to about 50 mm, or about 5 mm to about 30 mm, or about 10 mm to about 20 mm. The thickness of the plates (shown as 226 and 226' of plate 200 and 200', respectively, in FIGS. 4A and 4B) may be about 1 mm to about 15 mm, or about 2 mm to about 10 mm, or about 4 mm to about 8 mm. The fixation extensions may extend beyond the fixation surface by a distance (shown as 227 and 227' of plate 200 and 200', respectively, in FIGS. 4A and 4B) of about 0.5 to 5 mm, or about 1 to about 3 mm.

The plates may be of a material appropriate for implantation into the body. For instance, the material may be a metal such as titanium or cobalt chromium alloys; a biopolymer such as PEEK; a ceramic such as aluminum oxide or zirconia alloys; or a combination thereof.

Each plate comprises one or more appropriate-sized rare earth magnets. The one or more magnets may be embedded within the plates, such as embedded in the articulating surface of the superior plate and/or in the articulating surface of the inferior plate; however, the magnet(s) are not exposed to outside of the plate.

The shape of the magnets includes, but is not limited to, a shape that generally resembles a sphere, cylinder, hollow cylinder, ellipsoid, prism (e.g., cube, rectangular prism, triangular prism, pentagonal prism, hexagonal prism, etc.), hollow prism, pyramid, cone, torus, or other three-dimensional shapes known in the art. In some embodiments, more than one magnet may be present in a plate, such as in a configuration or array that provides the appropriate magnetic field for interacting with the magnet(s) of the other plate. If more than one magnet is present, the magnets may have any of the shapes described above, or portions thereof.

The magnets may comprise materials known in the art. For example, the magnets may be iron-based, nickel-based, cobalt-based, or an alloy of rare-earth metals. In certain embodiments, the magnets may be a rare-earth magnet, which generally has strong attraction and repulsion forces and have high retentive capacity and resistance to demagnification. In a preferred embodiment, the rare-earth magnet is an alloy of NdFeB.

The diameter or, in the case of a non-circular magnet, long axis (widest distance across) of the magnet(s) may be about 5 mm to about 30 mm, or about 10 mm to about 20 mm. The thickness of the magnet(s) plate may be about 0.5 mm to about 10 mm, or about 1 mm to about 6 mm.

One of ordinary skill in the art would be able to determine the arrangement of magnet(s) in the superior plate and magnet(s) in the inferior plate in order to achieve a prescribed magnetic force between the magnet(s) of the superior plate and the magnet(s) of the inferior plate, based upon the teachings in the Examples provided below. For example, the skilled artisan would understand from Example 1 the factors that impact the generated magnetic force, including magnet thickness, the magnet diameter, and the separation distance between the magnets, and understand the size of the magnets and arrangement of the magnets within the superior and inferior plates necessary to apply the prescribed force. Thus, the skilled artisan can determine how to arrange the magnets by considering the size and dimensions of the space of the disc that requires replacement, the type of force that is required for the treatment (e.g., a levitating force or a reducing force to decrease wear), as well as other factors such as the subject's weight, height, activity level, etc., which could all have an effect on loading forces experienced in the spine.

Two-Plate-with-Spacer Contacting Intervertebral Disc Replacement Device

An aspect of the invention relates to an intervertebral disc replacement device that comprises a superior plate, an inferior plate, and a spacer. Upon implantation, the superior plate is fixated to the adjacent vertebra superior to the disc that is being replaced, the inferior plate is fixated to the adjacent vertebra inferior to the disc that is being replaced, and the spacer is between the superior and inferior plates. Each plate contains one or more magnets embedded therein and optionally, the spacer may have one or more magnets embedded therein.

Without being bound by theory, an advantage of a two-plate-with-spacer contacting device may be the additional decrease in wear and generation of wear debris. In addition, the spacer may comprise one or more magnets that interact with the magnet(s) of the superior and/or inferior plates and decrease the separation distance between the magnet surfaces, therefore providing additional stability to the intervertebral disc replacement device.

Figure 5A:
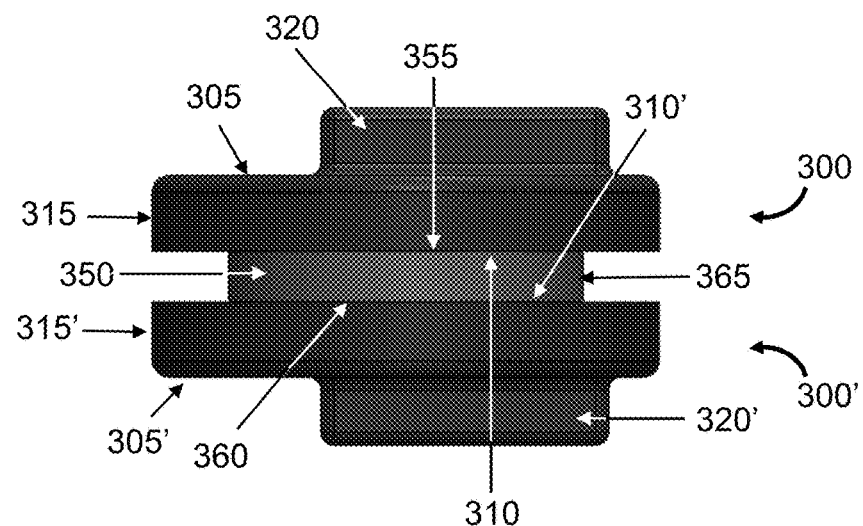
FIGS. 5A and 5B are different views of a two-plate-with-spacer contacting intervertebral disc replacement device according to embodiments of the present invention.
Figure 5B:
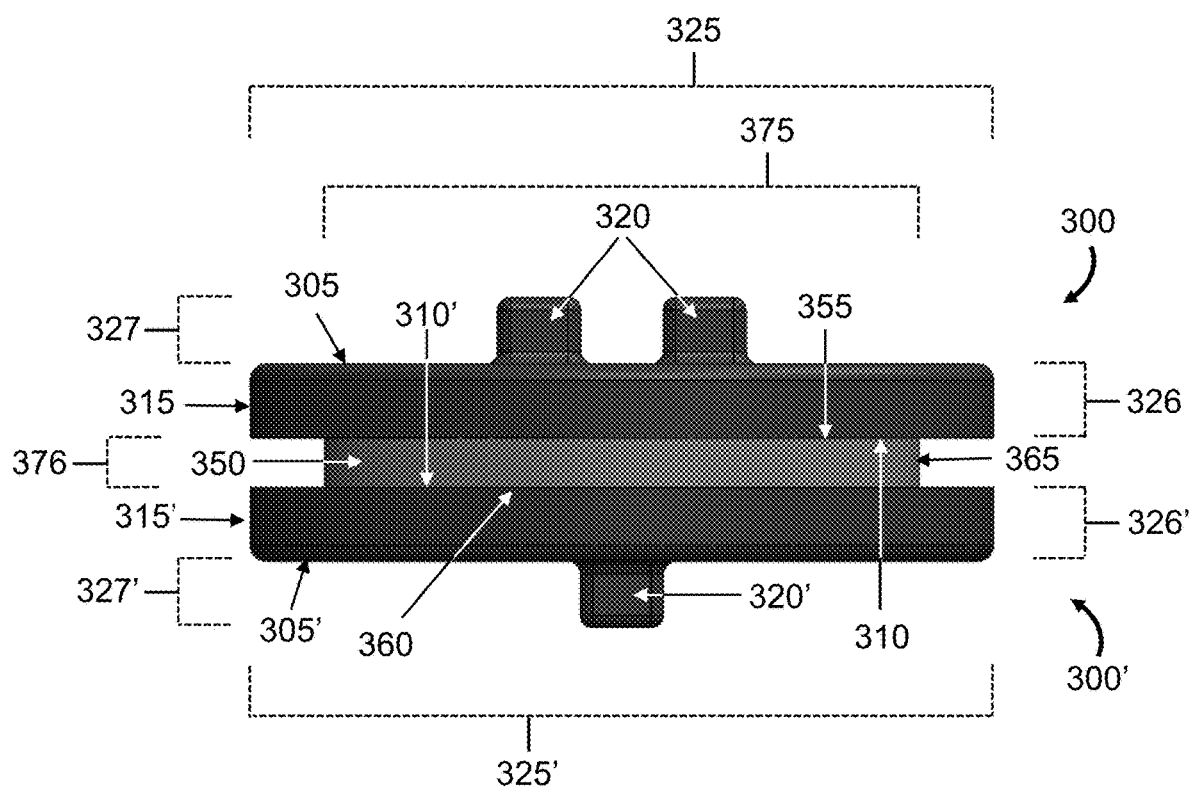
Figure 6A:
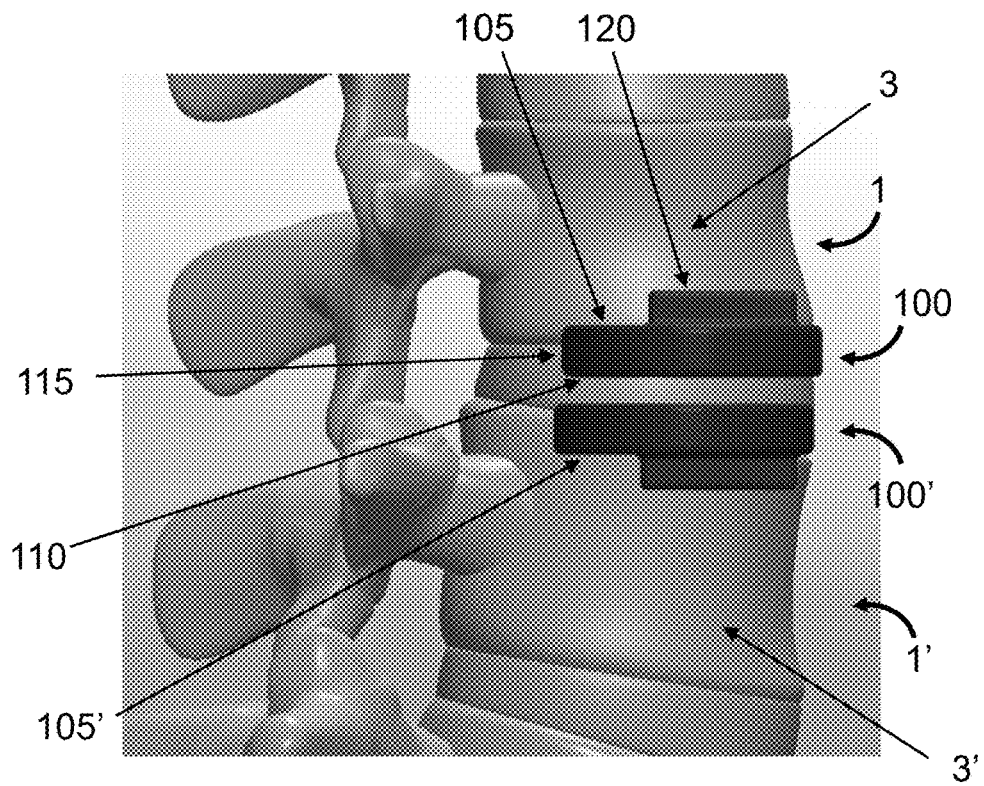
FIGS. 6A and 6B are different views of a two-plate non-contacting intervertebral disc replacement device according to embodiments of the present invention, implanted into a motion segment of a human spine.
Figure 6B:
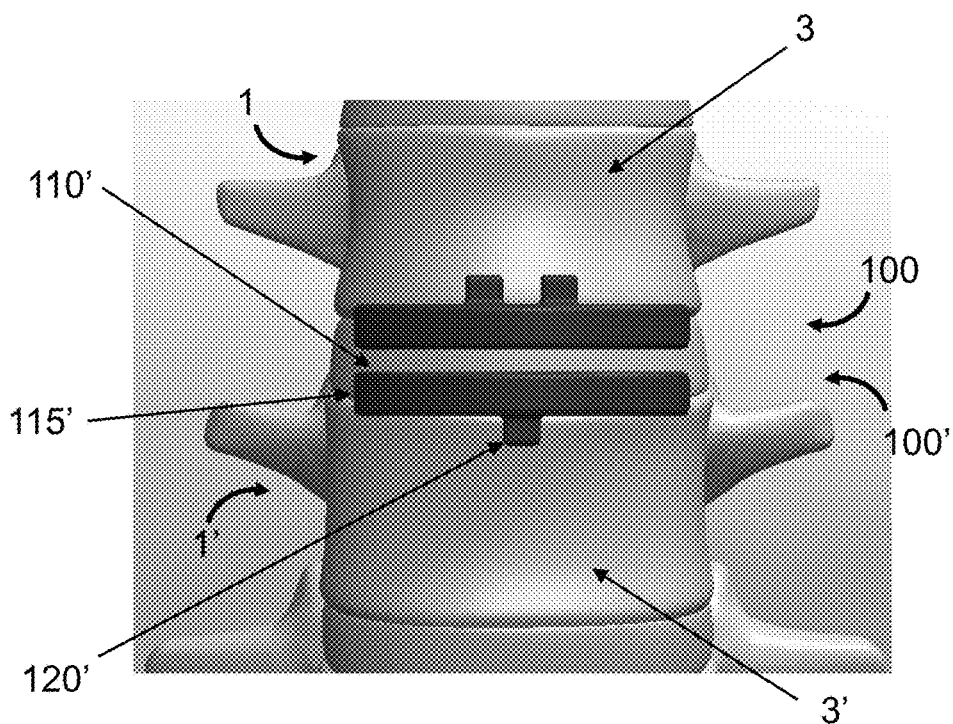

An example of a two-plate-with-spacer intervertebral disc replacement device according to embodiments of the invention is shown in FIGS. 5A and 5B. Superior plate 300 and inferior plate 300' may each comprise a fixation surface 305 and 305', respectively; an articulating surface 310 and 310', respectively; and an edge surface 315 and 315', respectively. Spacer 350 may comprise a superior articulating surface 355, an inferior articulating surface 360, and an edge surface 365. In embodiments of the invention, upon implantation as shown in FIGS. 12A-15B, fixation surface 305 and 305' may face the endplate of the vertebrae adjacent to the intervertebral disc that is being replaced, such that fixation surface 305 may face the endplate of vertebra 1 that is superior to the disc that is being replaced, and fixation surface 305' may face the endplate of vertebra 1' that is inferior to the intervertebral disc that is being replaced; superior articulating surface 355 of spacer 350 may form an articulating interface with articulating surface 310 of superior plate 300; and inferior articulating surface 360 of spacer 350 may form an articulating interface with articulating surface 310' of inferior plate 300'. Edge surface 315 and 315', and 365 is formed from the thickness of plates 300 and 300' and of spacer 350, respectively.

Each plate may also comprise a fixation extension that extends beyond the fixation surface of the plate. This is illustrated in FIGS. 5A and 5B, in which plate 300 and 300' comprises fixation extension 320 and 320', respectively. The fixation extension may comprise a single unit (see, e.g., fixation extension 320' of inferior plate 300' shown in FIG. 5B) or may comprise more than one unit (see, e.g., fixation extension 320 of superior plate 300 shown in FIG. 5A). Upon implantation, as shown for example in FIGS. 12A-15B, fixation extension 320 and 320' may form a surface that can adhere to the outside surface of vertebral body 3 and 3', respectively, of vertebra 1 and 1', respectively, that are adjacent to the intervertebral disc being replaced.

Each plate generally has the same shape, although that shape may vary. The plates may comprise a shape that generally resembles a sphere, cylinder, ellipsoid, prism (e.g., cube, rectangular prism, triangular prism, pentagonal prism, hexagonal prism, etc.), pyramid, cone, or other three-dimensional shapes known in the art. In some embodiments, each plate may comprise a cross-sectional shape that generally resembles the cross-sectional shape of the vertebral body portion of a vertebra.

In some embodiments, the plates may comprise a shape that resembles, is derived from, or is largely the same as, plates that are apart of intervertebral disc replacement devices known in the art. Such devices include those that are described in U.S. Pat. Nos. 6,001,130, 7,491,240, 7,494,508, 7,766,966, 8,353,964, 8,858,635, 8,911,498, 9,566,164, and 9,883,945, each of which are incorporated herein by reference.

The fixation surface of each plate (i) may be flat as shown in FIGS. 5A and 5B (see fixation surfaces 305 and 305'); (ii) may be curved (not shown); or (iii) a combination thereof (e.g., some portions of the surfaces are flat, while other portions are curved) (not shown). The fixation surface of the plates may comprise a surface geometry, a surface feature, or a combination thereof, that can help adhere the plates to the endplates of the vertebrae adjacent to the intervertebral disc that is being replaced. The surface geometry and/or surface feature may also provide initial stability and resistance to torsional or shear loading to plates. A surface geometry for the present invention may include, but is not limited to, a texture, porous coating, bioactive coating, and a combination thereof. A surface feature for the present invention may include, but is not limited to, one or more keels, one or more pegs, one or more screws, and the like, including a combination thereof.

The articulating surface of the superior plate and the superior articulating surface of the spacer may have conforming or near-conforming geometries to allow motion through articulation of these surfaces. The articulating surface of the inferior plate and the inferior articulating surface of the spacer may also have conforming or near-conforming geometries to allow motion through articulation of these surfaces. Examples of such conforming or near-conforming geometries include those resembling a ball-and-socket interface; a cup-and-dish interface; a flat-surface interface; toroidal-surface interface such as the surfaces described in U.S. Pat. No. 9,173,748, which is incorporated herein by reference; or the like.

The diameter or, in the case of a non-circular plate, long axis (widest distance across) of the plates (shown as 325 and 325' of plate 300 and 300', respectively, in FIGS. 5A and 5B) may be about 3 mm to about 50 mm, or about 5 mm to about 30 mm, or about 10 mm to about 20 mm. The thickness of the plates (shown as 326 and 326' of plate 300 and 300', respectively, in FIGS. 5A and 5B) may be about 1 mm to about 15 mm, or about 2 mm to about 10 mm, or about 4 mm to about 8 mm. The fixation extensions may extend beyond the fixation surface by a distance (shown as 327 and 327' of plate 300 and 300', respectively, in FIGS. 5A and 5B) of about 0.5 to 5 mm, or about 1 to about 3 mm.

The spacer may comprise a shape that generally resembles a sphere, cylinder, ellipsoid, prism (e.g., cube, rectangular prism, triangular prism, pentagonal prism, hexagonal prism, etc.), pyramid, cone, or other three-dimensional shapes known in the art. In some embodiments, the spacer may comprise a cross-sectional shape that generally resembles the cross-sectional shape of the superior and/or inferior plate. The diameter or, in the case of a non-circular spacer, long axis (widest distance across) of the spacer (shown as 375 of spacer 350 in FIGS. 5A and 5B) may be about 1 mm to about 48 mm, or about 2 mm to about 45 mm. The thickness of the spacer (shown as 376 of spacer 350 in FIGS. 5A and 5B) may be about 3 mm to about 25 mm, or about 5 mm to about 20 mm.

The plates and the spacer may be of a material appropriate for implantation into the body. For instance, the plates may comprise a metal such as titanium or cobalt chromium alloys; a biopolymer such as PEEK; a ceramic such as aluminum oxide or zirconia alloys; or a combination thereof. The spacer may comprise a polymer.

In embodiments of the present invention, each plate may comprise one or more appropriate-sized rare earth magnets and the spacer does not comprise a magnet. The one or more magnets may be embedded within the plates, such as embedded in the articulating surface of the superior plate and in the articulating surface of inferior plate; however, the magnet(s) are not exposed to outside of the plate. The magnet(s) of the superior plate and the magnet(s) of the inferior plate may be oriented such that a repulsive magnetic force exists between the magnet(s) of the superior plate and the magnet(s) of the inferior plate. Alternatively, the magnet(s) of the superior plate and the magnet(s) of the inferior plate may be oriented such that an attractive magnetic force exists between the magnet(s) of the superior plate and the magnet(s) of the inferior plate.

In other embodiments of the invention, each plate and the spacer may comprise one or more appropriate-sized rare earth magnets. The one or more magnets may be embedded within the plates, such as embedded in the articulating surface of the superior plate and in the articulating surface of the inferior plate, and may be embedded within the spacer. In certain embodiments the one or more magnets may be embedded in the superior articulating surface and/or in the inferior articular surface of the spacer; however, the magnet(s) are not exposed to outside of the plate or the spacer. In some embodiments, the magnet(s) embedded in the spacer may be oriented such that a repulsive magnetic force exists with the magnet(s) embedded in the superior plate and/or a repulsive magnetic force exists with the magnet(s) embedded in the inferior plate. As a result, each interface of two articulating surfaces experience a repulsive magnetic force in an effort to reduce contact stress and subsequent wear of the materials. In other embodiments, the magnet(s) embedded in the spacer may be oriented such that an attractive magnetic force exists with the magnet(s) embedded in the superior plate, and/or an attractive magnetic force exists with the magnet(s) embedded in the inferior plate. Thus, interfaces of two articulating surfaces can experience an attractive magnetic force in an effort to reduce the possibility of dislocation or dissociation of the spacer. Although not providing a wear reduction benefit, the reduction in dissociation risk is significant as this too is a major source of clinical failure. In further embodiments, the magnet(s) embedded in the spacer may be oriented such that a repulsive magnetic force exists with the magnet(s) embedded in the superior plate, and/or an attractive magnetic force exists with the magnet(s) embedded in the inferior plate. In yet other embodiments, the magnet(s) embedded in the spacer may be oriented such that an attractive magnetic force exists with the magnet(s) embedded in the superior plate, and/or a repulsive magnetic force exists with the magnet(s) embedded in the inferior plate.

The shape of the magnets includes, but is not limited to, a shape that generally resembles a sphere, cylinder, hollow cylinder, ellipsoid, prism (e.g., cube, rectangular prism, triangular prism, pentagonal prism, hexagonal prism, etc.), hollow prism, pyramid, cone, torus, or other three-dimensional shapes known in the art. In some embodiments, more than one magnet may be present in a plate or the spacer, such as in a configuration or array that provides the appropriate magnetic field for interacting with the magnet(s) of the other plate(s) and/or of the spacer. If more than one magnet is present, the magnets may have any of the shapes described above, or portions thereof.

The magnets may comprise materials known in the art. For example, the magnets may be iron-based, nickel-based, cobalt-based, or an alloy of rare-earth metals. In certain embodiments, the magnets may be a rare-earth magnet, which generally has strong attraction and repulsion forces and have high retentive capacity and resistance to demagnification. In a preferred embodiment, the rare-earth magnet is NdFeB.

The diameter or, in the case of a non-circular magnet, long axis (widest distance across) of the magnet(s) may be about 5 mm to about 30 mm, or about 10 mm to about 20 mm. The thickness of the magnet(s) plate may be about 0.5 mm to about 10 mm, or about 1 mm to about 6 mm.

One of ordinary skill in the art would be able to determine the arrangement of magnet(s) in the superior plate, magnet(s) in the inferior plate, and/or magnets in the spacer in order to achieve a prescribed magnetic force between or among the magnet(s) of the superior plate, the magnet(s) of the inferior plate, and/or the magnet(s) of the spacer, based upon the teachings in the Examples provided below. For example, the skilled artisan would understand from Example 1 the factors that impact the generated magnetic force, including magnet thickness, the magnet diameter, and the separation distance between the magnets, and understand the size of the magnets and arrangement of the magnets within the superior plate, inferior plate, and/or spacer necessary to apply the prescribed force. Thus, the skilled artisan can determine how to arrange the magnets by considering the size and dimensions of the space of the disc that requires replacement, the type of force that is required for the treatment (e.g., a levitating force or a reducing force to decrease wear), as well as other factors such as the subject's weight, height, activity level, etc., which could all have an effect on loading forces experienced in the spine.

Use of the Intervertebral Disc Replacement Devices

The devices of the present invention may be used to address or help treat health issues that require replacement of one or more intervertebral discs.

Therefore, aspects of the invention are directed to (i) a method of treating degenerative disc disease in an intervertebral disc, (ii) a method of relieving pain caused by degenerative disc disease in an intervertebral disc, and (iii) a method of reducing pain caused by degenerative disc disease in an intervertebral disc. Aspects of the invention are also directed to use of the intervertebral disc replacement devices according to embodiments of the present invention to (i) treat degenerative disc disease in an intervertebral disc, (ii) relieve pain caused by degenerative disc disease in an intervertebral disc, and (iii) reduce pain caused by degenerative disc disease in an intervertebral disc. Further aspects of the invention are directed to an intervertebral disc replacement devices according to embodiments of the present invention for use in (i) treating degenerative disc disease in an intervertebral disc, (ii) relieving pain caused by degenerative disc disease in an intervertebral disc, and (iii) reducing pain caused by degenerative disc disease in an intervertebral disc.

In embodiments of the invention, these methods and uses may comprise replacing the intervertebral disc subject to the degenerative disc disease, which involves removing the intervertebral disc, and implanting the device. In some embodiments, removal of the intervertebral disc comprises removing the disc material and annulus. In some embodiments, the method may further comprise denuding the cartilage endplates and preparing the surfaces of the endplates of the adjacent vertebrae. The result of implanting the device is a levitating force or a force to reduce wear, either of which can lead to treatment of degenerative disc disease in an intervertebral disc, relief of pain caused by degenerative disc disease in an intervertebral disc, and/or reduction of pain caused by degenerative disc disease in an intervertebral disc, as well as increased function.

In certain embodiments, the device is implanted by first exposing the disc space and inserting distracting pins in the vertebral bodies superior and inferior to the disc space. The joint may then be distracted using the pins for leverage and then a discectomy is performed whereby the annulus and nucleus, as well as the cartilage on the endplates of the vertebral bodies, are removed. The implant may then be trialed to determine the appropriate size implant and the actual implant placed in the disc space. The distraction may then be released and the implant may be put through a range of motion. The pins may then be removed and the wound is closed.

Implantation of devices of the invention are illustrated in FIGS. 6A-15B. FIGS. 6A-9B show a two-plate non-contacting intervertebral disc replacement device according to embodiments of the invention, implanted between vertebra 1 that is superior to the replaced disc and vertebra 1' that is inferior to the replaced disc. FIGS. 6A-7B show implantation of the device having no linking material between plates 100 and 100', in which FIGS. 7A and 7B show magnets 130 and 130' within plates 100 and 100', respectively. FIGS. 8A-9B show implantation of the device having a linking material 140 present between plates 100 and 100', in which FIGS. 9A and 9B show magnets 130 and 130' within plates 100 and 100', respectively. Separation distance 135 between magnet 130 of superior plate 100 and magnet 130' of inferior plate 100', as well as the size of magnets 130 and 130', are chosen so that a sufficient force is generated to maintain separation of the two vertebral bodies to normal physiology height or the desired separation height and the separation distance allows a normal range of motion in all planes or the desired range of motion (see, e.g., Example 1). In some embodiments of the invention, the two-plate non-contacting intervertebral disc replacement device is implanted such that distance 135 between magnet 130 and magnet 130' may be about 0.25 mm to about 20 mm, or about 0.5 mm to about 15 mm, or about 1 mm to about 10 mm.

FIGS. 10A-11B show a two-plate contacting intervertebral disc replacement device according to embodiments of the invention, implanted between vertebra 1 that is superior to the replaced disc and vertebra 1' that is inferior to the replaced disc. FIGS. 11A and 11B show magnets 230 and 230' within plates 100 and 100', respectively. Separation distance 235 between magnet 230 of superior plate 200 and magnet 230' of inferior plate 200', as well as the size of magnets 230 and 230', are chosen to reduce the contact stress and subsequent wear and debris generated since wear and debris generation is a function of load (see, e.g., Example 1). The load across articulating surfaces 210 and 210' of two plates 200 and 200', respectively, can be reduced as much as desired. In some embodiments of the invention, the two-plate contacting intervertebral disc replacement device is implanted such that distance 235 between magnet 230 and magnet 230' may be about 0.25 mm to about 20 mm, or about 0.5 mm to about 15 mm, or about 1 mm to about 10 mm.

FIGS. 12A-15B show a two-plate-with-spacer contacting intervertebral disc replacement device according to embodiments of the invention, implanted between vertebra 1 that is superior to the replaced disc and vertebra 1' that is inferior to the replaced disc. FIGS. 13A and 13B show magnets 330 and 330' of plates 300 and 300', respectively, upon implantation of a device according to embodiments in which spacer 350 does not have any magnets. Separation distance 335 is between magnet 330 of superior plate 300 and magnet 330' of inferior plate. FIGS. 14A and 14B show magnets 330 and 330' of plates 300 and 300', respectively, and magnet 370 of spacer 350 upon implantation of a device according to embodiments in which spacer 350 contains a magnet that is not in association with either of its superior articulating surface 355 or its inferior articulating surface 360. Separation distance 336 is between magnet 330 of superior plate 300 and magnet 370 of spacer 350, and separation distance 336' is between magnet 330' of inferior plate 300' and magnet 370 of the spacer 350. FIGS. 15A and 15B show magnets 330 and 330' of plates 300 and 300', respectively, and magnets 371 and 371' of spacer's articulating surfaces 355 and 360, respectively, upon implantation of a device according to embodiments in which spacer 350 contains a magnet 371 in association with its superior articulating surface 355 and contains a magnet 371' in association with its inferior articulating surface 360. Separation distance 337 between magnet 330 of superior plate 300 and magnet 371 associated with superior articulating surface 355 of spacer 350, and separation distance 337' between magnet 330' of inferior plate 300' and magnet 371' associated with inferior articulating surface 360 of spacer 350, as well as the size of magnets 330, 330', 370, 371, and 371', are chosen to either reduce the contact stress and subsequent wear and debris generated since wear and debris generation is a function of load (see, e.g., Example 1), or to generate a sufficient attractive magnetic force. The load across the articulating surfaces can be reduced as much as desired. In some embodiments of the invention, the two-plate-with-spacer contacting intervertebral disc replacement device is implanted such that distance 335, 336, 336', 337, and/or 337' may be about 0.25 mm to about 20 mm, or about 0.5 mm to about 15 mm, or about 1 mm to about 10 mm.

EXAMPLES

Example 1

A series of analyses were conducted using JMAG simulation technology to study how the magnetic repulsion forces are impacted by the magnet thickness, the magnet diameter, and the separation distance between the magnets. JMAG utilizes finite element analysis to calculate the magnetic forces and fields. Briefly, the geometry of the magnets is loaded into the simulation software, and the magnetic strength and pole orientation is assigned when the simulation is performed.

The analyses are designed to mimic the repulsion force generated between the magnet of a superior plate and the magnet of an inferior plate in a two-plate non-contacting intervertebral disc replacement device according to embodiments of the present invention; or between the magnet of a superior plate and the magnet of an inferior plate in a two-plate contacting intervertebral disc replacement device according to embodiments of the present invention; or between the magnet of a superior/inferior plate and the magnet of a spacer in a two-plate-with-spacer contacting intervertebral disc replacement device, according to embodiments of the present invention. The analyses considered magnet thicknesses of 3 mm and 5 mm; magnet diameters of 10 mm, 15 mm, 20 mm, and 25 mm; and separation distances of 0.25 mm, 0.5 mm, 1 mm, 3 mm, 5 mm, 7 mm, and 10 mm.

The analyses show that, in general, a greater magnet diameter results in a greater repulsion force between the magnets (see Tables 1 and 2, and FIGS. 16 and 17). In addition, a greater magnet thickness generates a greater repulsion force between the magnets (see Table 3 and FIG. 18). Further, for each magnet thickness and magnet diameter, an increase in separation distance between the magnets led to a decrease in repulsion force.

These results demonstrate how the magnet thickness, the magnet diameter, and the separation distance between magnets in the plates/spacer can all impact the magnetic repulsion forces that are generated.

TABLE 1

Repulsion forces generated between the magnets of the disc replacement devices for variations in magnet diameter and separation distance and with a 3 mm magnet thickness.

| Separation Distance | Magnet Diameter (mm) | | | |
|---|---|---|---|---|
| (mm) | 10 | 15 | 20 | 25 |
| 1 | 14.1N | 24.1N | 34.1N | 44.1N |
| 3 | 6.1N | 12.4N | 18.2N | 24.2N |
| 5 | 3.0N | 6.9N | 11.0N | 15.8N |
| 7 | 1.4N | 4.4N | 7.4N | 10.8N |
| 10 | 0.5N | 2.0N | 4.0N | 6.5N |

TABLE 2

Repulsion forces generated between the magnets of the disc replacement devices for variations in magnet diameter and separation distance and with a 5 mm magnet thickness.

| Separation Distance | Magnet Diameter (mm) | | | |
|---|---|---|---|---|
| (mm) | 10 | 15 | 20 | 25 |
| 1 | 22.1N | 40.7N | 61.0N | 83.0N |
| 3 | 10.3N | 22.8N | 35.8N | 49.7N |
| 5 | 5.5N | 13.7N | 23.5N | 33.6N |
| 7 | 3.0N | 8.7N | 16.2N | 23.8N |
| 10 | 1.1N | 4.4N | 9.4N | 15.4N |

TABLE 3

Repulsion forces generated between the magnets of the disc replacement devices for variations in magnet thickness and separation distance and with a 25 mm magnet diameter.

| Separation Distance | Magnet Thickness (mm) | |
|---|---|---|
| (mm) | 3 | 5 |
| 0.25 | 65.8N | 112.8N |
| 0.5 | 56.4N | 100.9N |
| 1 | 44.1N | 83.0N |
| 3 | 24.2N | 49.7N |
| 5 | 15.8N | 33.6N |
| 7 | 10.8N | 23.8N |
| 10 | 6.5N | 15.4N |

Example 2

A finite element analysis was conducted using JMAG as described in Example 1 to study how the magnetic repulsion forces are impacted by motion between the superior plate and inferior plate of an intervertebral disc replacement device. In particular, the analysis assesses the magnetic force field that is generated when the angle between the plates, and therefore the angle between the magnets that are embedded therein, is at 7°.

The analysis shows that a greater repulsive magnetic force is generated at the ends of the magnet that are closer together, as compared to the ends of the magnet that are more separated (see FIGS. 19 and 20). Such results demonstrate that, upon implantation, as motion occurs the plates will move closer together, which brings the opposing poles of the magnets closer together and a greater repulsive resistance force may be generated. This resistance force may limit the motion and prevents extreme motion and contact between the surfaces.

The foregoing description is given for clearness of understanding only, and no unnecessary limitations should be understood therefrom, as modifications within the scope of the invention may be apparent to those having ordinary skill in the art.

Detailed embodiments of the present intervertebral disc replacement devices and methods thereof are disclosed herein; however, it is to be understood that the disclosed embodiments are merely illustrative of the intervertebral disc replacement device and methods that may be embodied in various forms. In addition, each of the examples given in connection with the various embodiments of the systems and methods are intended to be illustrative, and not restrictive.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where devices are described as including plates, spacers, and/or materials, it is contemplated that the compositions can also consist essentially of, or consist of, any combination of the recited plates, spacers, and/or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various steps may be changed without departing from the scope or spirit of the method, unless described otherwise. In addition, some of the individual steps can be combined, omitted, or further subdivided into additional steps.

All patents, publications and references cited herein are hereby fully incorporated by reference. In case of conflict between the present disclosure and incorporated patents, publications and references, the present disclosure should control.

What is claimed is:

1. A method of treating a degenerative disc disease in an intervertebral disc between a superior vertebra and an inferior vertebra, comprising removing the intervertebral disc, and implanting an intervertebral disc replacement device comprising a superior plate and an inferior plate, wherein:
    the superior plate is adhered to the superior vertebra and the inferior plate is adhered to the inferior vertebra;
    each of the superior plate and the inferior plate comprises one or more magnets embedded therein, wherein the one or more magnets in the superior plate and the one or more magnets in the inferior plate are oriented such that a repulsive magnetic force exists between the one or more magnets in the superior plate and the one or more magnet in the inferior plate;
    each of the superior plate and the inferior plate comprises a fixation extension, wherein the fixation extension of the superior plate is configured to adhere to the outer surface of the vertebral body of the superior vertebra, and the fixation extension of the inferior plate is configured to adhere to the outer surface of the vertebral body of the inferior vertebra;
    the superior plate and the inferior plate are separated by a distance, and the superior plate and the inferior plate each do not have an articulating surface;
    no spacer is present between the superior plate and the inferior plate; and
    the superior plate and the inferior plate each contain (i) one magnet, or (ii) more than one magnet.

2. The method of claim 1, wherein the superior plate and the inferior plate comprise a material selected from the group consisting of a metal, a biopolymer, a ceramic, and a combination thereof.

3. The method of claim 1, wherein the one or more magnets in the superior plate and the one or more magnets in the inferior plate comprise a material that is iron-based, nickel-based, cobalt-based, or an alloy of rare-earth metals.

4. The method of claim 3, wherein the one or more magnets in the superior plate and the one or more magnets in the inferior plate comprise an alloy of neodymium, iron, and boron.

5. The method of claim 1, wherein the superior plate and the inferior plate each comprise a fixation surface and an inner surface.

6. The method of claim 5, wherein the fixation surface of the superior plate and the fixation surface of the inferior plate each comprise a surface geometry, a surface feature, or a combination thereof.

7. The method of claim 6, wherein the surface geometry is selected from the group consisting of a texture, porous coating, bioactive coating, and a combination thereof.

8. The method of claim 6 wherein the surface feature is selected from the group consisting of one or more keels, one or more pegs, one or more screws, and a combination thereof.

9. An intervertebral disc replacement device for treating degenerative disc disease in an intervertebral disc between a superior vertebra and an inferior vertebra, the intervertebral disc replacement device comprising a superior plate and an inferior plate, wherein:
    each of the superior plate and the inferior plate comprises one or more magnets embedded therein, wherein the one or more magnets in the superior plate and the one or more magnets in the inferior plate are oriented such that a repulsive magnetic force exists between the one or more magnets in the superior plate and the one or more magnets in the inferior plate;
    each of the superior plate and the inferior plate comprises a fixation extension, wherein the fixation extension of the superior plate is configured to adhere to the outer surface of the vertebral body of the superior vertebra, and the fixation extension of the inferior plate is configured to adhere to the outer surface of the vertebral body of the inferior vertebra;
    the superior plate and the inferior plate are separated by a distance, and the superior plate and the inferior plate each do not have an articulating surface;
    no spacer is present between the superior plate and the inferior plate; and
    the superior plate and the inferior plate each contain (i) one magnet, or (ii) more than one magnet.

10. The intervertebral disc replacement device of claim 9, wherein the superior plate and the inferior plate each comprise a fixation surface and an inner surface.

11. The intervertebral disc replacement device of claim 10, wherein the fixation surface of the superior plate and the fixation surface of the inferior plate each comprise a surface geometry, a surface feature, or a combination thereof.

12. The intervertebral disc replacement device of claim 11, wherein the surface geometry is selected from the group consisting of a texture, porous coating, bioactive coating, and a combination thereof.

13. The intervertebral disc replacement device of claim 11, wherein the surface feature is selected from the group consisting of one or more keels, one or more pegs, one or more screws, and a combination thereof.

14. The intervertebral disc replacement device of claim 9, wherein the superior plate and the inferior plate comprise a material selected from the group consisting of a metal, a biopolymer, a ceramic, and a combination thereof.

* * * * *